US007611846B2

(12) United States Patent
Yu et al.

(10) Patent No.: US 7,611,846 B2
(45) Date of Patent: Nov. 3, 2009

(54) DIAGNOSTIC METHODS INVOLVING HUMAN GROWTH FACTOR HUXAG-1

(75) Inventors: Guo-Liang Yu, Berkeley, CA (US); Patrick J. Dillon, Carlsbad, CA (US); Reinhard Ebner, Gaithersburg, MD (US); Gregory A. Endress, Florence, MA (US)

(73) Assignee: Human Genome Sciences, Inc., Rockville, MD (US)

( * ) Notice: Subject to any disclaimer, the term of this patent is extended or adjusted under 35 U.S.C. 154(b) by 416 days.

(21) Appl. No.: 11/368,664

(22) Filed: Mar. 7, 2006

(65) Prior Publication Data

US 2006/0205654 A1 Sep. 14, 2006

Related U.S. Application Data

(60) Division of application No. 10/922,101, filed on Aug. 20, 2004, now Pat. No. 7,060,801, which is a division of application No. 10/078,337, filed on Feb. 21, 2002, now Pat. No. 6,818,412, which is a continuation of application No. 09/362,870, filed on Jul. 29, 1999, now abandoned, which is a division of application No. 08/916,576, filed on Aug. 22, 1997, now Pat. No. 6,171,816.

(60) Provisional application No. 60/024,347, filed on Aug. 23, 1996.

(51) Int. Cl.
*G01N 33/53* (2006.01)
*C07K 16/00* (2006.01)
*A61K 38/27* (2006.01)

(52) U.S. Cl. .................. 435/7.1; 530/387.9; 530/399
(58) Field of Classification Search ........................ None
See application file for complete search history.

(56) References Cited

U.S. PATENT DOCUMENTS

| 5,770,384 | A | 6/1998 | Androphy et al. |
| 5,792,833 | A | 8/1998 | Androphy et al. |
| 6,171,816 | B1 | 1/2001 | Yu et al. |
| 7,060,801 | B2 | 6/2006 | Yu et al. |

FOREIGN PATENT DOCUMENTS

| WO | WO 96/19566 A1 | 6/1996 |
| WO | WO 98/11217 A2 | 3/1998 |
| WO | WO 98/41627 A1 | 9/1998 |
| WO | WO 98/46756 A1 | 10/1998 |
| WO | WO 99/06548 A | 2/1999 |

OTHER PUBLICATIONS

Adam, P.J., et al., "Comprehensive Proteomic Analysis of Breast Cancer Cell Membranes Reveals Unique Proteins with Potential Roles in Clinical Cancer," *J. Biol. Chem.* 278:6482-6489, The American Society for Biochemistry and Molecular Biology, Inc. (Feb. 2003).

Andersson, B., et al., "A 'Double Adaptor' Method for Improved Shotgun Library Construction," *Anal. Biochem.* 236:107-113, Academic Press, Inc. (Apr. 1996).

Ausubel, F.M., et al., "Screening Recombinant DNA Libraries," in: *Short Protocols in Molecular Biology*, Ausubel, F.M., et al., eds., John Wiley & Sons, Inc., New York, New York, pp. 185-191 (1989).

Callard, R.E. and Gearing, A.J.H., "3. The cytokine network," in: *The Cytokine FactsBook*, Callard, R.E. and Gearing, A.J.H., eds., Academic Press, Inc., San Diego, California, pp. 12-17, 119, 185, 214 and 252 (1994).

Database EMBL, Accession No. U76752, Sive, H., et al., European Molecular Biology Laboratory (Dec. 1996).

Database EMBL, Accession No. O42251, Sive, H.L., et al., European Molecular Biology Laboratory (Jan. 1998).

Database EMBL, Accession No. AAY12312, Dumas Milne Edwards, J., et al., European Molecular Biology Laboratory (Jun. 1999).

Database EMBL, Accession No. AAX41145, Dumas Milne Edwards, J., et al., European Molecular Biology Laboratory (Jun. 1999).

Drysdale, T.A. and Elinson, R.P., "Cell Migration and Induction in the Development of the Surface Ectodermal Pattern of the *Xenopus laevis* Tadpole," *Develop. Growth & Differ.* 34:51-59, Japanese Society of Developmental Biologists (1992).

Fletcher, G.C., et al., "hAG-2 and hAG-3, human homologues of genes involved in differentiation, are associated with oestrogen receptor-positive breast tumours and interact with metastasis gene C4.4a and dystroglycan," *Brit. J. Cancer* 88:579-585, Nature Publishing Group (Feb. 2003).

Folz, R.J., et al., "Substrate Specificity of Eukaryotic Signal Peptidase. Site-Saturation Mutagenesis at Position -1 Regulates Cleavage Between Multiple Sites in Human Pre(ΔPRO)Apolipoprotein A-II," *J. Biol. Chem.* 263:2070-2078, The American Society for Biochemistry and Molecular Biology, Inc (1988).

International Search Report for International Patent Application No. PCT/US96/13766, mailed Jan. 7, 1997.

International Search Report for International Patent Application No. PCT/US97/14139, mailed Nov. 17, 1997.

(Continued)

*Primary Examiner*—Gary B Nickol
*Assistant Examiner*—Bruce D Hissong
(74) *Attorney, Agent, or Firm*—Sterne, Kessler, Goldstein & Fox P.L.L.C.

(57) ABSTRACT

The present invention relates to huXAG-1, huXAG-2 and huXAG-3 proteins which are novel human growth factors. In particular, isolated nucleic acid molecules are provided encoding the huXAG-1, huXAG-2 and huXAG-3 proteins. huXAG-1, huXAG-2 and huXAG-3 polypeptides are also provided as are vectors, host cells and recombinant methods for producing the same. The invention further relates to screening methods for identifying agonists and antagonists of huXAG-1, huXAG-2 or huXAG-3 activity. Also provided are diagnostic and therapeutic uses of huXAG-1, huXAG-2 and huXAG-3.

20 Claims, 10 Drawing Sheets

OTHER PUBLICATIONS

Jamrich, M. And Sato, S., "Differential gene expression in the anterior neural plate during gastrulation of *Xenopus laevis*," *Development* 105:779-786, Company of Biologists Ltd. (1989).

Keesee, S.K., et al., "Nuclear matrix proteins in human colon cancer," *Proc. Natl. Acad. Sci. USA* 91:1913-1916, National Academy of Sciences (1994).

NCBI Entrez, GenBank Report, Accession No. T24475, from Frigerio, J.-M., et al., National Center for Biotechnology Information (Sep. 1994).

NCBI Entrez, GenBank Report, Accession No. T24892, from Frigerio, J.-M., et al., National Center for Biotechnology Information (Sep. 1994).

NCBI Entrez, GenBank Report, Accession No. Z46177, from Auffray, C., et al., National Center for Biotechnology Information (Nov. 1994).

NCBI Entrez, GenBank Report, Accession No. T31098, from Adams, M.D., et al., National Center for Biotechnology Information (Sep. 1995).

NCBI Entrez, GenBank Report, Accession No. T81278, from Hillier, L., et al., National Center for Biotechnology Information (Mar. 1995).

NCBI Entrez, GenBank Report, Accession No. T86663, from Hillier, L., et al., National Center for Biotechnology Information (Mar. 1995).

NCBI Entrez, GenBank Report, Accession No. T94936, from Hillier, L., et al., National Center for Biotechnology Information (Mar. 1995).

NCBI Entrez, GenBank Report, Accession No. T94990, from Hillier, L., et al., National Center for Biotechnology Information (Mar. 1995).

NCBI Entrez, GenBank Report, Accession No. R23553, from Hillier, L., et al., National Center for Biotechnology Information (Apr. 1995).

NCBI Entrez, GenBank Report, Accession No. R46892, from Matsuki, Y., et al., National Center for Biotechnology Information (May 1995).

NCBI Entrez, GenBank Report, Accession No. H35621, from Lee, N.H., et al., National Center for Biotechnology Information (Jul. 1995).

NCBI Entrez, GenBank Report, Accession No. H66313, from Hillier, L., et al., National Center for Biotechnology Information (Oct. 1995).

NCBI Entrez, GenBank Report, Accession No. D75170, from Kohara, Y., et al., National Center for Biotechnology Information (Dec. 1995).

NCBI Entrez, GenBank Report, Accession No. D75830, from Kohara, Y., et al., National Center for Biotechnology Information (Dec. 1995).

NCBI Entrez, GenBank Report, Accession No. D80998, from Fujiwara, T., et al., National Center for Biotechnology Information (Feb. 1996).

NCBI Entrez, GenBank Report, Accession No. W03932, from Hillier, L., et al., National Center for Biotechnology Information (Apr. 1996).

NCBI Entrez, GenBank Report, Accession No. W11310, from Marra, M., et al., National Center for Biotechnology Information (Apr. 1996).

NCBI Entrez, GenBank Report, Accession No. W11794, from Marra, M., et al., National Center for Biotechnology Information (Apr. 1996).

NCBI Entrez, GenBank Report, Accession No. W15466, from Hillier, L., et al., National Center for Biotechnology Information (May 1996).

NCBI Entrez, GenBank Report, Accession No. W37614, from Hillier, L., et al., National Center for Biotechnology Information (May 1996).

NCBI Entrez, GenBank Report, Accession No. W39620, from Hillier, L., et al., National Center for Biotechnology Information (May 1996).

NCBI Entrez, GenBank Report, Accession No. W44207, from Marra, M., et al., National Center for Biotechnology Information (May 1996).

NCBI Entrez, GenBank Report, Accession No. W47880, from Marra, M., et al., National Center for Biotechnology Information (May 1996).

NCBI Entrez, GenBank Report, Accession No. W48140, from Marra, M., et al., National Center for Biotechnology Information (May 1996).

NCBI Entrez, GenBank Report, Accession No. G19689, from Adams, M.D., National Center for Biotechnology Information (May 1996).

NCBI Entrez, GenBank Report, Accession No. G23839 from Hudson, T., National Center for Biotechnology Information (May 1996).

NCBI Entrez, GenBank Report, Accession No. AA030653, from Marra, M., et al., National Center for Biotechnology Information (Aug. 1996).

NCBI Entrez, GenBank Report, Accession No. AA034623, from Marra, M., et al., National Center for Biotechnology Information (Aug. 1996).

NCBI Entrez, GenBank Report, Accession No. AA044518, from Marra, M., et al., National Center for Biotechnology Information (Sep. 1996).

NCBI Entrez, GenBank Report, Accession No. G28839, from Smith, M.W., et al., National Center for Biotechnology Information (Sep. 1996).

NCBI Entrez, GenBank Report, Accession No. W87967, from Marra, M., et al., National Center for Biotechnology Information (Sep. 1996).

NCBI Entrez, GenBank Report, Accession No. W89817, from Marra, M., et al., National Center for Biotechnology Information (Sep. 1996).

NCBI Entrez, GenBank Report, Accession No. C08511, from Kohara, Y., et al., National Center for Biotechnology Information (Sep. 1996).

NCBI Entrez, GenBank Report, Accession No. C10047, from Kohara, Y., et al., National Center for Biotechnology Information (Sep. 1996).

NCBI Entrez, GenBank Report, Accession No. AA108028, from Marra, M., et al., National Center for Biotechnology Information (Nov. 1996).

NCBI Entrez, GenBank Report, Accession No. AAB18819 from Sive, H.L., et al., National Center for Biotechnology Information (Nov. 1996).

NCBI Entrez, GenBank Report, Accession No. AA055880, from Hillier, L., et al., National Center for Biotechnology Information (Dec. 1996).

NCBI Entrez, GenBank Report, Accession No. AA139704, from Marra, M., et al., National Center for Biotechnology Information (Dec. 1996).

NCBI Entrez, GenBank Report, Accession No. AA115712, from Hillier, L., et al., National Center for Biotechnology Information (Dec. 1996).

NCBI Entrez, GenBank Report, Accession No. AA194085 from Hillier, L., et al., National Center for Biotechnology Information (Dec. 1996).

NCBI Entrez, GenBank Report, Accession No. AA421562, from Hillier, L., et al., National Center for Biotechnology Information (Dec. 1996).

NCBI Entrez, GenBank Report, Accession No. AA220662, from Marra, M., et al., National Center for Biotechnology Information (Feb. 1997).

NCBI Entrez, GenBank Report, Accession No. AA230334, from Marra, M., et al., National Center for Biotechnology Information (Feb. 1997).

NCBI Entrez, GenBank Report, Accession No. AA244356, from National Cancer Institute, Cancer Genome Anatomy Project (CGAP), Tumor Gene Index, National Center for Biotechnology Information (Mar. 1997).

NCBI Entrez, GenBank Report, Accession No. AA248602, from Liew, C.C., National Center for Biotechnology Information (Mar. 1997).

NCBI Entrez, GenBank Report, Accession No. AA250084, from Marra, M., et al., National Center for Biotechnology Information (Mar. 1997).

NCBI Entrez, GenBank Report, Accession No. AA266163, from Marra, M., et al., National Center for Biotechnology Information (Mar. 1997).
NCBI Entrez, GenBank Report, Accession No. AA271241, from Marra, M., et al., National Center for Biotechnology Information (Mar. 1997).
NCBI Entrez, GenBank Report, Accession No. AA272445, from Marra, M., et al., National Center for Biotechnology Information (Mar. 1997).
NCBI Entrez, GenBank Report, Accession No. AA274540, from Marra, M., et al., National Center for Biotechnology Information (Mar. 1997).
NCBI Entrez, GenBank Report, Accession No. AA297756, from Adams, M.D., et al., National Center for Biotechnology Information (Apr. 1997).
NCBI Entrez, GenBank Report, Accession No. AA298710, from Adams, M.D., et al., National Center for Biotechnology Information (Apr. 1997).
NCBI Entrez, GenBank Report, Accession No. AA297933, from Adams, M.D., et al., National Center for Biotechnology Information (Apr. 1997).
NCBI Entrez, GenBank Report, Accession No. AA307513, from Adams, M.D., et al., National Center for Biotechnology Information (Apr. 1997).
NCBI Entrez, GenBank Report, Accession No. AA307697, from Adams, M.D., et al., National Center for Biotechnology Information (Apr. 1997).
NCBI Entrez, GenBank Report, Accession No. AA307795, from Adams, M.D., et al., National Center for Biotechnology Information (Apr. 1997).
NCBI Entrez, GenBank Report, Accession No. AA313235, from Adams, M.D., et al., National Center for Biotechnology Information (Apr. 1997).
NCBI Entrez, GenBank Report, Accession No. AA314146, from Adams, M.D., et al., National Center for Biotechnology Information (Apr. 1997).
NCBI Entrez, GenBank Report, Accession No. AA314206, from Adams, M.D., et al., National Center for Biotechnology Information (Apr. 1997).
NCBI Entrez, GenBank Report, Accession No. AA314225, from Adams, M.D., et al., National Center for Biotechnology Information (Apr. 1997).
NCBI Entrez, GenBank Report, Accession No. AA314372, from Adams, M.D., et al., National Center for Biotechnology Information (Apr. 1997).
NCBI Entrez, GenBank Report, Accession No. AA315049, from Adams, M.D., et al., National Center for Biotechnology Information (Apr. 1997).
NCBI Entrez, GenBank Report, Accession No. AA315166, from Adams, M.D., et al., National Center for Biotechnology Information (Apr. 1997).
NCBI Entrez, GenBank Report, Accession No. AA315613, from Adams, M.D., et al., National Center for Biotechnology Information (Apr. 1997).
NCBI Entrez, GenBank Report, Accession No. AA315629, from Adams, M.D., et al., National Center for Biotechnology Information (Apr. 1997).
NCBI Entrez, GenBank Report, Accession No. AA315724, from Adams, M.D., et al., National Center for Biotechnology Information (Apr. 1997).
NCBI Entrez, GenBank Report, Accession No. AA316115, from Adams, M.D., et al., National Center for Biotechnology Information (Apr. 1997).
NCBI Entrez, GenBank Report, Accession No. AA316233, from Adams, M.D., et al., National Center for Biotechnology Information (Apr. 1997).
NCBI Entrez, GenBank Report, Accession No. AA316874, from Adams, M.D., et al., National Center for Biotechnology Information (Apr. 1997).
NCBI Entrez, GenBank Report, Accession No. AA316967, from Adams, M.D., et al., National Center for Biotechnology Information (Apr. 1997).
NCBI Entrez, GenBank Report, Accession No. AA410501, from Hillier, L., et al., National Center for Biotechnology Information (May 1997).
NCBI Entrez, GenBank Report, Accession No. AA425142, from Hillier, L., et al., National Center for Biotechnology Information (May 1997).
NCBI Entrez, GenBank Report, Accession No. AA426228, from Hillier, L., et al., National Center for Biotechnology Information (May 1997).
NCBI Entrez, GenBank Report, Accession No. AA437001, from Hillier, L., et al., National Center for Biotechnology Information (May 1997).
NCBI Entrez, GenBank Report, Accession No. AA442829, from Hillier, L., et al., National Center for Biotechnology Information (Jun. 1997).
NCBI Entrez, GenBank Report, Accession No. AA469767, from Marra, M., et al., National Center for Biotechnology Information (Jun. 1997).
NCBI Entrez, GenBank Report, Accession No. AA473910, from Marra, M., et al., National Center for Biotechnology Information (Jun. 1997).
NCBI Entrez, GenBank Report, Accession No. AA476675, from Hillier, L., et al., National Center for Biotechnology Information (Jun. 1997).
NCBI Entrez, GenBank Report, Accession No. AA498120, from Marra, M., et al., National Center for Biotechnology Information (Jul. 1997).
NCBI Entrez, GenBank Report, Accession No. AA498578, from Marra, M., et al., National Center for Biotechnology Information (Jul. 1997).
NCBI Entrez, GenBank Report, Accession No. AA509472, from Marra, M., et al., National Center for Biotechnology Information (Jul. 1997).
NCBI Entrez, GenBank Report, Accession No. AA512381, from Marra, M., et al., National Center for Biotechnology Information (Jul. 1997).
NCBI Entrez, GenBank Report, Accession No. AA538512, from Marra, M., et al., National Center for Biotechnology Information (Jul. 1997).
NCBI Entrez, GenBank Report, Accession No. AA533047, from National Cancer Institute, Cancer Genome Anatomy Project, National Center for Biotechnology Information (Aug. 1997).
NCBI Entrez, GenBank Report, Accession No. AA552670, from National Cancer Institute, Cancer Genome Anatomy Project, National Center for Biotechnology Information (Sep. 1997).
NCBI Entrez, GenBank Report, Accession No. AA565444, from National Cancer Institute, Cancer Genome Anatomy Project, National Center for Biotechnology Information (Sep. 1997).
NCBI Entrez, GenBank Report, Accession No. AA565996, from National Cancer Institute, Cancer Genome Anatomy Project, National Center for Biotechnology Information (Sep. 1997).
NCBI Entrez, GenBank Report, Accession No. AA573742, from National Cancer Institute, Cancer Genome Anatomy Project, National Center for Biotechnology Information (Sep. 1997).
NCBI Entrez, GenBank Report, Accession No. AA581848, from National Cancer Institute, Cancer Genome Anatomy Project, National Center for Biotechnology Information (Sep. 1997).
NCBI Entrez, GenBank Report, Accession No. AA582017, from National Cancer Institute, Cancer Genome Anatomy Project, National Center for Biotechnology Information (Sep. 1997).
NCBI Entrez, GenBank Report, Accession No. AA582851, from National Cancer Institute, Cancer Genome Anatomy Project, National Center for Biotechnology Information (Sep. 1997).
NCBI Entrez, GenBank Report, Accession No. AA583091, from National Cancer Institute, Cancer Genome Anatomy Project, National Center for Biotechnology Information (Sep. 1997).
NCBI Entrez, GenBank Report, Accession No. AA593818, from National Cancer Institute, Cancer Genome Anatomy Project, National Center for Biotechnology Information (Sep. 1997).
NCBI Entrez, GenBank Report, Accession No. AA607599, from Marra, M., et al., National Center for Biotechnology Information (Sep. 1997).

NCBI Entrez, GenBank Report, Accession No. AA622524, from National Cancer Institute, Cancer Genome Anatomy Project, National Center for Biotechnology Information (Oct. 1997).

NCBI Entrez, GenBank Report, Accession No. AA632103, from National Cancer Institute, Cancer Genome Anatomy Project, National Center for Biotechnology Information (Oct. 1997).

NCBI Entrez, GenBank Report, Accession No. AA638538, from Marra, M., et al., National Center for Biotechnology Information (Oct. 1997).

NCBI Entrez, GenBank Report, Accession No. AA691538, from Marra, M., et al., National Center for Biotechnology Information (Dec. 1997).

NCBI Entrez, GenBank Report, Accession No. AA710639, from Marra, M., et al., National Center for Biotechnology Information (Dec. 1997).

NCBI Entrez, GenBank Report, Accession No. AA776960, from Hillier, L., et al., National Center for Biotechnology Information (Feb. 1998).

NCBI Entrez, GenBank Report, Accession No. AAC77358 from Thompson, D.A., National Center for Biotechnology Information (Oct. 1998).

NCBI Entrez, GenBank Report, Accession No. AR022361 from Androphy, E.J. and D.E. Breiding, National Center for Biotechnology Information (Dec. 1998).

NCBI Entrez, GenBank Report, Accession No. AAD20035, from Mei, G., et al., National Center for Biotechnology Information (Feb. 1999).

NCBI Entrez, GenBank Report, Accession No. AF131758 from Mei, G., et al., National Center for Biotechnology Information (Mar. 1999).

NCBI Entrez, GenBank Report, Accession No. AC002400 from Adams, M.D., National Center for Biotechnology Information (Nov. 1999).

NCBI Entrez, GenBank Report, Accession No. BAA32044 from Komiya, T. and S. Hirohashi, National Center for Biotechnology Information (Nov. 1999).

NCBI Entrez, GenBank Report, Accession No. AL079342 from Tromans, A., National Center for Biotechnology Information (Feb. 2000).

NCBI Entrez, GenBank Report, Accession No. AAF39830 from R. Waterston, National Center for Biotechnology Information (Mar. 2000).

NCBI Entrez, GenBank Report, Accession No. CAB55026 from Smye, R., National Center for Biotechnology Information (Dec. 2001).

Pan, M., et al., "Tumor Necrosis Factor Stimulates System x-AG Transport Activity in Human Endothelium," *J. Surg. Res.* 58:659-664, Academic Press, Inc. (Jun. 1995).

Pending U.S. Appl. No. 09/912,293, Rosen et al., Not Published: pp. 1-75 (pp. 1+2 partially redacted); portion of Table 2; and SEQ ID Nos. 50802 and 171241.

Sive, H.L., et al., "Progressive Determination during Formation of the Anteroposterior Axis in *Xenopus laevis*," Cell 58:171-180, Cell Press (1989).

Sive, H. and Bradley, L., "A Sticky Problem: The *Xenopus* Cement Gland as a Paradigm for Anteroposterior Patterning," *Developmental Dynamics* 205:265-280, Wiley-Liss, Inc. (Mar. 1996).

Supplementary Partial European Search Report for Application No. EP 97 92 4803, completed Mar. 26, 2004.

Thompson, D.A., and Weigel, R.J., "hAG-2, the Human Homologue of the *Xenopus laevis* Cement Gland Gene XAG-2, Is Coexpressed with Estrogen Receptor in Breast Cancer Cell Lines," *Biochem. Biophys. Res. Commun.* 251:111-116, Academic Press (Oct. 1998).

von Heijne, G., "A new method for predicting signal sequence cleavage sites," *Nucleic Acids Research* 14:4683-4690, IRL Press Limited, Oxford England (1986).

Yu, W., et al., "Large-Scale Concatenation cDNA Sequencing," *Genome Res.* 7:353-358, Cold Spring Harbor Laboratory Press (Apr. 1997).

```
          10                  30                  50
CGAGCGGCACGAGCCGATTCCTAGCCGCCGACTCACACAAGGCAGGTGGGTGAGGAAATC 70                  90                 110
CAGAGTTGCCATGGAGAAAATTCCAGTGTCAGCATTCTTGCTCCTTGTGGCCCTCTCCTA
             M  E  K  I  P  V  S  A  F  L  L  L  V  A  L  S  Y 130                 150                 170
CACTCTGGCCAGAGATACCACAGTCAAACCTGGAGCCAAAAAGGACACAAAGGACTCTCG
 T  L  A  R  D  T  T  V  K  P  G  A  K  K  D  T  K  D  S  R 190                 210                 230
ACCCAAACTGCCCCAGACCCTCTCCAGAGGTTGGGGTGACCAACTCATCTGGACTCAGAC
 P  K  L  P  Q  T  L  S  R  G  W  G  D  Q  L  I  W  T  Q  T 250                 270                 290
ATATGAAGAAGCTCTATATAAATCCAAGACAAGCAACAAACCCTTGATGATTATTCATCA
 Y  E  E  A  L  Y  K  S  K  T  S  N  K  P  L  M  I  I  H  H 310                 330                 350
CTTGGATGAGTGCCCACACAGTCAAGCTTTAAAGAAAGTGTTTGCTGAAAATAAAGAAAT
 L  D  E  C  P  H  S  Q  A  L  K  K  V  F  A  E  N  K  E  I 370                 390                 410
CCAGAAATTGGCAGAGCAGTTTGTCCTCCTCAATCTGGTTTATGAAACAACTGACAAACA
 Q  K  L  A  E  Q  F  V  L  L  N  L  V  Y  E  T  T  D  K  H 430                 450                 470
CCTTTCTCCTGATGGCCAGTATGTCCCCAGGATTATGTTTGTTGACCCATCTCTGACAGT
 L  S  P  D  G  Q  Y  V  P  R  I  M  F  V  D  P  S  L  T  V 490                 510                 530
TAGAGCCGATATCACTGGAAGATATTCAAATCGTCTCTATGCTTACGAACCTGCAGATAC
 R  A  D  I  T  G  R  Y  S  N  R  L  Y  A  Y  E  P  A  D  T 550                 570                 590
AGCTCTGTTGCTTGACAACATGAAGAAAGCTCTCAAGTTGCTGAAGACTGAATTGTAAAG
 A  L  L  L  D  N  M  K  K  A  L  K  L  L  K  T  E  L  *

610                 630                 650
AAAAAAAATCTCCAAGCCCTTCTGTCTGTCAGGCCTTGAGACTTGAAACCAGAAGAAGTG
         670                 690                 710
TGAGAAGACTGGCTAGTGTGGAAGCATAGTGAACACACTGATTAGGTTATGGTTTAATGT
         730                 750                 770
TACAACAACTATTTTTTAAGAAAAACAAGTTTTAGAAATTTGGTTTCAAGTGTACATGTG
         790                 810                 830
TGAAAACAATATTGTATACTACCATAGTGAGCCATGATTTTCTAAAAAAAAAAAATAAATG
         850                 870
TTTTGGGGGTGTTCTGTTTTCTCCCAAAAAAAAAA
```

FIG.1

```
                  10                    30                    50
        GAGCGGCGCTCGGCGAACTGTGTGGACCGTCTGCTGGGACTCCGGCCCTGCGTCCGCTCA 70                    90                   110
        GCCCCGTGGCCCCGCGCACCTACTGCCATGGAGACGCGGCCTCGTCTCGGGGCCACCTGT
                                          MetGluThrArgProArgLeuGlyAlaThrCys 130                   150                   170
        TTGCTGGGCTTCAGTTTCCTGCTCCTCGTCATCTCTTCTGATGGACATAATGGGCTTGGA
        LeuLeuGlyPheSerPheLeuLeuLeuValIleSerSerAspGlyHisAsnGlyLeuGly 190                   210                   230
        AAGGGTTTTGGAGATCATATTCATTGGAGGACACTGGAAGATGGGAAGAAAGAAGCAGCT
        LysGlyPheGlyAspHisIleHisTrpArgThrLeuGluAspGlyLysLysGluAlaAla 250                   270                   290
        GCCAGTGGACTGCCCCTGATGGTGATTATTCATAAATCCTGGTGTGGAGCTTGCAAAGCT
        AlaSerGlyLeuProLeuMetValIleIleHisLysSerTrpCysGlyAlaCysLysAla 310                   330                   350
        CTAAAGCCCAAATTTGCAGAATCTACGGAAATTTCAGAACTCTCCCATAATTTTGTTATG
        LeuLysProLysPheAlaGluSerThrGluIleSerGluLeuSerHisAsnPheValMet 370                   390                   410
        GTAAATCTTGAGGATGAAGAGGAACCCAAAGATGAAGATTTCAGCCCTGACGGGGGTTAT
        ValAsnLeuGluAspGluGluGluProLysAspGluAspPheSerProAspGlyGlyTyr 430                   450                   470
        ATTCCACGAATCCTTTTTCTGGATCCCAGTGGCAAGGTGCATCCTGAAATCATCAATGAG
        IleProArgIleLeuPheLeuAspProSerGlyLysValHisProGluIleIleAsnGlu 490                   510                   530
        AATGGAAACCCCAGCTACAAGTATTTTTATGTCAGTGCCGAGCAAGTTGTTCAGGGGATG
        AsnGlyAsnProSerTyrLysTyrPheTyrValSerAlaGluGlnValValGlnGlyMet 550                   570                   590
        AAGGAAGCTCAGGAAAGGCTGACGGGTGATGCCTTCAGAAAGAAACATCTTGAAGATGAA
        LysGluAlaGlnGluArgLeuThrGlyAspAlaPheArgLysLysHisLeuGluAspGlu
```

FIG.2A

```
       610                  630                  650
TTGTAACATGAATGTGCCCCTTCTTTCATCAGAGTTAGTGTTCTGGAAGGAAAGCAGCAG
LeuEnd
       670                  690                  710
GGAAGGGAATATTGAGGAATCATCTAGAACAATTAAGCCGACCAGGAAACCTCATTCCTA
       730                  750                  770
CCTACACTGGAAGGAGCGCTCTCACTGTGGAAGAGTTCTGCTAACAGAAGCTGGTCTGCA
       790                  810                  830
TGTTTGTGGATCCAGCGGAGAGTGGCAGACTTTCTTCTCCTTTTCCCTCTCACCTAAATG
       850                  870                  890
TCAACTTGTCATTGAATGTAAAGAATGAAACCTTCTGACACAAAACTTGAGCCACTTGGA
       910                  930                  950
TGTTTACTCCTCGCACTTAAGTATTTGAGTCTTTTCCCATTTCCTCCCACTTTACTCACC
       970                  990                  1010
TTAGTGGTGAAAGGAGACTAGTAGCATCTTTTCTACAACGTTAAAATTGCAGAAGTAGCT
       1030                 1050                 1070
TATCATTAAAAAACAACAACAACAACAATAACAATAAATCCTAAGTGTAAATCAGTTATT
       1090                 1110                 1130
CTACCCCCTACCAAGGATATCAGCCTGTTTTTTCCCTTTTTTCTCCTGGGAATAATTGTG
       1150                 1170                 1190
GGCTTCTTCCCAAATTTCTACAGCCTCTTTCCTCTTCTCATGCTTGAGCTTCCCTGTTTG
       1210                 1230                 1250
CACGCATGCGTGTGCAGGACTGGCTGTGTGCTTGGACTCGGCTCCAGGTGGAAGCATGCT
       1270                 1290                 1310
TTCCCTTGTTACTGTTGGAGAAACTCAAACCTTCAAGCCCTAGGTGTAGCCATTTTGTCA
       1330                 1350                 1370
AGTCATCAACTGTATTTTTGTACTGGCATTAACAAAAAAGAGATAAAATATTGTACCAT
       1390                 1410
TAAACTTTAATAAAACTTTAAAAGGAAAAAAAAAAAAAAAAAAA
```

FIG.2B

```
          10                    30                    50
CAAGAGCACTGGCCAAGTCAGCTTCTTCTGAGAGAGTCTCTAGAAGACATGATGCTACAC
                                                    MetMetLeuHis 70                    90                   110
TCAGCTTTGGGTCTCTGCCTCTTACTCGTCACAGTTTCTTCCAACCTTGCCATTGCAATA
SerAlaLeuGlyLeuCysLeuLeuLeuValThrValSerSerAsnLeuAlaIleAlaIle 130                   150                   170
AAAAAGGAAAAGAGGCCTCCTCAGACACTCTCAAGAGGATGGGGAGATGACATCACTTGG
LysLysGluLysArgProProGlnThrLeuSerArgGlyTrpGlyAspAspIleThrTrp 190                   210                   230
GTACAAACTTATGAAGAAGGTCTCTTTTATGCTCAAAAAAGTAAGAAGCCATTAATGGTT
ValGlnThrTyrGluGluGlyLeuPheTyrAlaGlnLysSerLysLysProLeuMetVal 250                   270                   290
ATTCATCACCTGGAGGATTGTCAATACTCTCAAGCACTAAAGAAAGTATTTGCCCAAAAT
IleHisHisLeuGluAspCysGlnTyrSerGlnAlaLeuLysLysValPheAlaGlnAsn 310                   330                   350
GAAGAAATACAAGAAATGGCTCAGAATAAGTTCATCATGCTAAACCTTATGCATGAAACC
GluGluIleGlnGluMetAlaGlnAsnLysPheIleMetLeuAsnLeuMetHisGluThr 370                   390                   410
ACTGATAAGAATTTATCACCTGATGGGCAATATGTGCCTAGAATCATGTTTGTAGACCCT
ThrAspLysAsnLeuSerProAspGlyGlnTyrValProArgIleMetPheValAspPro 430                   450                   470
TCTTTAACAGTTAGAGCTGACATAGCTGGAAGATACTCTAACAGATTGTACACATATGAG
SerLeuThrValArgAlaAspIleAlaGlyArgTyrSerAsnArgLeuTyrThrTyrGlu 490                   510                   530
CCTCGGGATTTACCCCTATTGATAGAAAACATGAAGAAAGCATTAAGACTTATTCAGTCA
ProArgAspLeuProLeuLeuIleGluAsnMetLysLysAlaLeuArgLeuIleGlnSer 550                   570                   590
GAGCTATAAGAGATGATAGAAAAAAGCCTTCACTTCAAAGAAGTCAAATTTCATGAAGAA
GluLeuEnd
```

FIG.3A

```
           610                   630                    650
AACCTCTGGCACATTGACAAATACTAAATGTGCAAGTATATAGATTTTGTAATATTACTA
           670                   690                    710
TTTAGTTTTTTTTAATGTGTTTGCAATAGTCTTATTAAAATAAATGTTTTTTAAAAAAAA
           730
AAAAAAAAAAAA
```

FIG.3B

```
              M E X X X X L G A - C L L L V - - A L S X X L A - - X X X K   Majority
                       10              20              30
   1   M Q A G L S L - V - C V L L C S A L G E A V L K K P K K Q  xeXAG.aa
   1   M E - K I P V S A - F L L L V - - A L S Y T L A R D T T V K  huXAG-1.aa
   1   M E T R P R L G A T C L L - - - - G F S F L L L - - - - -   huXAG-2.aa
   1   M M L H S A L G L - C L L L V - - T V S S N L A - - I A I K  huXAG-3.aa

- G - - - - - K D X R P - - I - - K G P Q T L S R G W G D X  Majority
                       40              50              60
  29   A G T T D T K T D Q E P A P I K T K G L K T L D R G W G E S  xeXAG.aa
  27   P G A K K D T K D S R P - - - - K L P Q T L S R G W G D Q  huXAG-1.aa
  21   - - - - - - - - - - - V I S S D G H N G L G K G F G D H  huXAG-2.aa
  26   - - - - - - - K E K R P - - - - - - P Q T L S R G W G D D  huXAG-3.aa I X W V Q T Y E E G L X K A X X S N K P L M V I H H L E D C  Majority
                       70              80              90
  59   I E W V Q T Y E E G L A K R E N N K P L M V I H H L E D C  xeXAG.aa
  52   L I W T Q T Y E E A L Y K S K T S N K P L M I I H H L D E C  huXAG-1.aa
  38   I H W - R T L E D G K K E A A S G L P L M V I I H K S W C  huXAG-2.aa
  42   I T W V Q T Y E E G L F Y A Q K S K K P L M V I H H L E D C  huXAG-3.aa P Y S Q A L K K V F A E N X E I Q E L A Q N - F V M L N L V  Majority
                       100             110             120
  89   P Y S I A L K K A F V A D R M A Q K L A Q E D F I M L N L V  xeXAG.aa
  82   P H S Q A L K K V F A E N K E I Q K L A E Q - F V L L N L V  huXAG-1.aa
  67   G A C K A L K P K F A E S T E I S E L S H N - F V M V N L E  huXAG-2.aa
  72   Q Y S Q A L K K V F A Q N E E I Q E M A Q N K F T M L N L M  huXAG-3.aa
```

FIG.4A

```
            H E T T - - D E N L S P D G Q Y V P R I M F V D P S L T V R  Majority
                      130             140                 150
      119   H P V A - - D E N Q S P D G H Y V P R V I F I D P S L T V R   xeXAG.aa
      111   Y E T T - - D K H L S P D G Q Y V P R I M F V D P S L T V R   huXAG-1.aa
       96   D E E E P K D E D F S P D G Y I P R I L F L D P S G K V H    huXAG-2.aa
      102   H E T T - - D K N L S P D G Q Y V P R I M F V D P S L T V R   huXAG-3.aa A D I X G R Y G N R L Y A Y E P X D X P L L I X N M K K A -  Majority
                      160             170                 180
      147   S D L K G R Y G N K M Y A Y D A D D I P E L I T N M K K A -   xeXAG.aa
      139   A D I T G R Y S N R L Y A Y E P A D T A L L L D N M K K A -   huXAG-1.aa
      126   P E I I N E N G N P S Y K Y F Y V S A E Q V V Q G M K E A Q   huXAG-2.aa
      130   A D I A G R Y S N R L Y T Y E P R D L P L L I E N M K K A -   huXAG-3.aa

- - - - - - - - - L K L L K T E L X                          Majority
                              190
      176   - - - - - - - - - K S F L K T E L - L                         xeXAG-.aa
      168   - - - - - - - - - L K L L K T E L                             huXAG-1.aa
      156   E R L T G D A F R K K H L E D E L                             huXAG-2.aa
      159   - - - - - - - - - L R L I Q S E L                             huXAG-3.aa
```

DIAGNOSTIC METHODS INVOLVING HUMAN GROWTH FACTOR HUXAG-1

CROSS-REFERENCE TO RELATED APPLICATIONS

The present application is a division of U.S. patent application Ser. No. 10/922,101, filed Aug. 20, 2004, now U.S. Pat. No. 7,060,801 B2; said application is a division of U.S. patent application Ser. No. 10/078,337, filed Feb. 21, 2002, now U.S. Pat. No. 6,818,412; said application Ser. No. 10/078,337, is a continuation of U.S. application Ser. No. 09/362,870, filed Jul. 29, 1999, now abandoned; said application Ser. No. 09/362,870, is a divisional of U.S. application Ser. No. 08/916,576, filed Aug. 22, 1997, now U.S. Pat. No. 6,171,816; said application Ser. No. 08/916,576, claims priority benefit to U.S. application Ser. No. 60/024,347, filed Aug. 23, 1996, the disclosure of which is herein incorporated by reference.

BACKGROUND OF THE INVENTION

1. Field of the Invention

The present invention relates to novel human growth factors. More specifically, isolated nucleic acid molecules are provided encoding huXAG-1, huXAG-2, and huXAG-3. HuXAG-1, huXAG-2, and huXAG-3 polypeptides are also provided, as are vectors, host cells and recombinant methods for producing the same. The invention further relates to screening methods for identifying agonists and antagonists of huXAG-1, huXAG-2, and huXAG-3 activity, as well as diagnostic and therapeutic uses of huXAG-1, huXAG-2 and huXAG-3.

2. Related Art

Growth Factors

Control of cell division is a basic aspect of multicellular existence that depends upon a programmed series of events. One factor in cellular proliferation and its control that has been identified is the presence of various polypeptide growth factors. Growth factors are essential components of growth media for in vitro cell culture and are involved in cell survival in vivo. Some of the growth factors that have been identified to date include PDGF (platelet-derived growth factor) implicated in the repair of the vascular system in vivo; EGF (epidermal growth factor) which acts as a mitogen for cells of ectodermal and mesodermal origin; TGF-a (transforming growth factor) which acts as a mitogen similarly to EGF but can make normal cells grow in agar; TGF-b (transforming growth factor) which is a mitogen for some cells and a growth inhibitor for others; and NGF (nerve growth factor) involved in the development and maintenance of sympathetic and embryonic neurons. Watson et al., Molecular Biology of the Gene, p. 975 (Benjamin/Cummings 1987).

It is clear that particular cell types require particular growth factors. Peptide growth factors are produced and secreted from a variety of tissues. The target cells are typically located close to the site of release of the growth factor (paracrine response). In addition to their growth promoting and differentiation-inducing activities, growth factors elicit a wide variety of effects in their target cells and are involved in processes such as inflammation, immune reactions and wound repair. See, Pimentel, E. *Handbook of Growth Factors, Volume 1: General Basics* (CRC Press 1994).

Monitoring of growth factor gene expression in cells of various human tissue, would be useful in detecting and studying abnormal hypertrophy both in vitro and in vivo. In addition, monitoring for higher than normal expression of tissue-specific growth factors would be useful in early diagnosis of certain cancers.

Additionally, polypeptide growth factors are very important cell culture reagents for stimulating cellular growth and aiding survival of the cells in vitro.

The search continues to exist for polypeptides that stimulate and/or inhibit growth of particular cells for both in vitro and in vivo uses. In addition, the search continues for novel tissue specific markers that can be employed qualitatively to help identify a particular cell or tissue type and employed qualitatively to assess whether cells, tissues or organs are abnormal in their expression of a particular polypeptide.

At the front of the larvae in most frog species lies a small and sticky patch of cells, called the cement gland. The cement gland lies anterior to the brain and any other neural tissue and develops from the embryonic ectoderm (Drysdale et al., *Dev. Growth Differ.* 34:51-59 (1992)). Formation of the cement gland is influenced by multiple signals (Sive et al., *Dev. Dyn.* 205:265-280 (1996)). One such signal is the XAG protein, which is expressed at very high levels in the cement gland and at lower levels in the more posterior hatching gland. It encodes a secreted protein later expressed in the pharynx (Jamrich et al., *Development* 105:779-786 (1989)) and in the lung primordium.

Colorectal Carcinoma

Colorectal carcinoma is a cancer which affects many people per year. The prognosis is poor in about 50% of the cases because the tumor is often not detected until the disease has spread and has reached a terminal stage. Early diagnosis is important to increase chances of arresting the carcinoma before it metastasizes, thereby leading to an improved prognosis.

One method of early tumor diagnosis is detection of the presence of a marker or antigen specific for a particular tumor. These normally proteinaceous markers are synthesized by the tumor, and may be found in the serum and/or on the surface of the tumor. Only a limited number of tumor markers for colorectal carcinoma have thus far been found to have clinical use. These include carcinoembryonic antigen (CEA), and the sialyated Lewis a antigen (CA 19.9). Unfortunately, approximately 40% of patients whose condition has been accurately diagnosed as colorectal carcinoma do not have elevated plasma levels of either of these antigens when initially examined. There is a need for commercially available serodiagnostic markers which can be used to detect the tumor and to monitor therapy for this group.

Another method of diagnosis involves detecting the presence of a gene associated with a particular disease or condition. A need exists for genetic markers which can be detected by genetic screening tests for the early detection of colon cancer in high risk patients.

Accordingly, it is an object of this invention to provide a new marker for the detection of colorectal carcinoma.

It is another object of the invention to provide a new marker suitable for diagnosing and monitoring colorectal cancer. Such novel marker can be further used to make novel antibodies or other antagonists that bind the colon cancer specific polypeptides to diagnose cancer and to bind and inhibit the biological function of the polypeptide.

A further object of the present invention is to provide a method and kit for the detection and monitoring of colorectal carcinoma in patients using assay methods specific for markers associated with colorectal carcinoma cells.

SUMMARY OF THE INVENTION

The present invention provides a novel group of isolated nucleic acid molecules that encode for human growth factors. The growth factors are small secreted proteins that exhibit a good degree of sequence similarity to one another.

The present invention provides isolated nucleic acid molecules comprising a polynucleotide encoding the huXAG-1 (also referred to as colon cancer-specific gene (CCSG)) polypeptide having the amino acid sequence shown in SEQ ID NO:2 or the amino acid sequence encoded by the cDNA clone deposited as ATCC Deposit Number 97641 on Jun. 27, 1996. The nucleotide sequence was determined by sequencing the deposited huXAG-1 clone and is shown in SEQ ID NO:1. The sequence contains an open reading frame encoding a polypeptide of about 175 amino acid residues, with a leader sequence of about 20 amino acid residues, and a predicted molecular weight of about 20 kDa. The amino acid sequence of mature huXAG-1 is shown in SEQ ID NO:2 (amino acid residues from about 1 to about 155 in SEQ ID NO:2).

Thus, one aspect of the invention provides an isolated nucleic acid molecule comprising a polynucleotide having a nucleotide sequence selected from the group consisting of: (a) a nucleotide sequence encoding the huXAG-1 polypeptide having the complete amino acid sequence in SEQ ID NO:2; (b) a nucleotide sequence encoding the huXAG-1 polypeptide having the complete amino acid sequence in SEQ ID NO:2 but minus the N-terminal methionine residue; (c) a nucleotide sequence encoding the mature huXAG-1 having the amino acid sequence at positions from about 1 to about 155 in SEQ ID NO:2; (d) a nucleotide sequence encoding the huXAG-1 polypeptide having the complete amino acid sequence encoded by the cDNA clone contained in ATCC Deposit No. 97641; (e) a nucleotide sequence encoding the mature huXAG-1 polypeptide having the amino acid sequence encoded by the cDNA clone contained in ATCC Deposit No. 97641; and (f) a nucleotide sequence complementary to any of the nucleotide sequences in (a), (b), (c), (d), or (e) above.

The present invention also provides isolated nucleic acid molecules comprising a polynucleotide encoding the huXAG-2 polypeptide having the amino acid sequence shown in SEQ ID NO:4 or the amino acid sequence encoded by the cDNA deposited as ATCC Deposit Number 209134 on Jun. 27, 1997. The nucleotide sequence determined by sequencing the deposited huXAG-2 clone, which is shown in SEQ ID NO:3, contains an open reading frame encoding a polypeptide of about 172 amino acid residues, with a leader sequence of about 23 amino acid residues. The amino acid sequence of the mature huXAG-2 is shown in SEQ ID NO:4 (amino acid residues from about 1 to about 149 in SEQ ID NO:4).

Thus, another aspect of the invention provides an isolated nucleic acid molecule comprising a polynucleotide having a nucleotide sequence selected from the group consisting of: (a) a nucleotide sequence encoding the huXAG-2 polypeptide having the complete amino acid sequence in SEQ ID NO:4; (b) a nucleotide sequence encoding the huXAG-2 polypeptide having the complete amino acid sequence in SEQ ID NO:4 but minus the N-terminal methionine residue; (c) a nucleotide sequence encoding the mature huXAG-2 having the amino acid sequence at positions from about 1 to about 149 in SEQ ID NO:4; (d) a nucleotide sequence encoding the huXAG-2 polypeptide having the complete amino acid sequence encoded by the cDNA clone contained in ATCC Deposit No. 209134; (e) a nucleotide sequence encoding the mature huXAG-2 polypeptide having the amino acid sequence encoded by the cDNA clone contained in ATCC Deposit No. 209134; and (f) a nucleotide sequence complementary to any of the nucleotide sequences in (a), (b), (c), (d), or (e) above.

The present invention also provides isolated nucleic acid molecules comprising a polynucleotide encoding the huXAG-3 polypeptide having the amino acid sequence shown in SEQ ID NO:6 or the amino acid sequence encoded by the cDNA deposited as ATCC Deposit Number 209137 on Jul. 3, 1997. The nucleotide sequence determined by sequencing the deposited huXAG-3 clone, which is shown in SEQ ID NO:5, contains an open reading frame encoding a polypeptide of about 166 amino acid residues, with a leader sequence of about 23 amino acid residues. The amino acid sequence of the mature huXAG-3 receptor is shown in SEQ ID NO:6 (amino acid residues from about 1 to about 143 in SEQ ID NO:6).

Thus, another aspect of the invention provides an isolated nucleic acid molecule comprising a polynucleotide having a nucleotide sequence selected from the group consisting of: (a) a nucleotide sequence encoding the huXAG-3 polypeptide having the complete amino acid sequence in SEQ ID NO:6; (b) a nucleotide sequence encoding the huXAG-3 polypeptide having the complete amino acid sequence in SEQ ID NO:6 but minus the N-terminal methionine residue; (c) a nucleotide sequence encoding the mature huXAG-3 having the amino acid sequence at positions from about 1 to about 143 in SEQ ID NO:6; (d) a nucleotide sequence encoding the huXAG-3 polypeptide having the complete amino acid sequence encoded by the cDNA clone contained in ATCC Deposit No. 209137; (e) a nucleotide sequence encoding the mature huXAG-3 polypeptide having the amino acid sequence encoded by the cDNA clone contained in ATCC Deposit No. 209137; and (f) a nucleotide sequence complementary to any of the nucleotide sequences in (a), (b), (c), (d), or (e) above.

Further embodiments of the invention include isolated nucleic acid molecules that comprise a polynucleotide having a nucleotide sequence at least 95% identical, and more preferably at least 96%, 97%, 98% or 99% identical, to any of the nucleotide sequences of huXAG-1, huXAG-2 or huXAG-3 in (a), (b), (c), (d), (e), or (f), above, or a polynucleotide which hybridizes under stringent hybridization conditions to a polynucleotide in (a), (b), (c), (d), (e), or (f), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a huXAG-1, huXAG-2, or huXAG-3 polypeptide having an amino acid sequence in (a), (b), (c), (d), or (e), above.

The present invention also relates to recombinant vectors, which include the isolated nucleic acid molecules of the present invention, and to host cells containing the recombinant vectors, as well as to methods of making such vectors and host cells and for using them for production of huXAG-1, huXAG-2, or huXAG-3 polypeptides or peptides by recombinant techniques.

The invention further provides an isolated huXAG-1 polypeptide having an amino acid sequence selected from the group consisting of: (a) the amino acid sequence of the huXAG-1 polypeptide having the complete 175 amino acid sequence, including the leader sequence shown in SEQ ID NO:2; (b) the amino acid sequence of the huXAG-1 polypeptide having the complete 175 amino acid sequence, including the leader sequence shown in SEQ ID NO:2 but minus the N-terminal methionine residue; (c) the amino acid sequence of the mature huXAG-1 polypeptide (without the leader) having the amino acid sequence at positions 1-155 in SEQ ID NO:2; (d) the amino acid sequence of the huXAG-1 polypeptide having the complete amino acid sequence, including the leader, encoded by the cDNA clone contained in ATCC Deposit No. 97641; and (e) the amino acid sequence of the mature huXAG-1 polypeptide having the amino acid sequence encoded by the cDNA clone contained in ATCC Deposit No. 97641.

The invention further provides an isolated huXAG-2 polypeptide having an amino acid sequence selected from the group consisting of: (a) the amino acid sequence of the huXAG-2 polypeptide having the complete 172 amino acid sequence, including the leader sequence shown in SEQ ID NO:4; (b) the amino acid sequence of the huXAG-2 polypeptide having the complete 172 amino acid sequence, including the leader sequence shown in SEQ ID NO:4 but minus the N-terminal methionine residue; (c) the amino acid sequence of the mature huXAG-2 polypeptide (without the leader) having the amino acid sequence at positions 1-149 in SEQ ID NO:4; (d) the amino acid sequence of the huXAG-2 polypeptide having the complete amino acid sequence, including the leader, encoded by the cDNA clone contained in ATCC Deposit No. 209134; and (e) the amino acid sequence of the mature huXAG-2 polypeptide having the amino acid sequence encoded by the cDNA clone contained in ATCC Deposit No. 209134.

The invention also provides an isolated huXAG-3 polypeptide having an amino acid sequence selected from the group consisting of: (a) the amino acid sequence of the huXAG-3 polypeptide having the complete 166 amino acid sequence, including the leader sequence shown in SEQ ID NO:6; (b) the amino acid sequence of the huXAG-3 polypeptide having the complete 166 amino acid sequence, including the leader sequence shown in SEQ ID NO:6 but minus the N-terminal methionine residue; (c) the amino acid sequence of the mature huXAG-3 polypeptide (without the leader) having the amino acid sequence at positions 1-143 in SEQ ID NO:6; (d) the amino acid sequence of the huXAG-3 polypeptide having the complete amino acid sequence, including the leader, encoded by the cDNA clone contained in ATCC Deposit No. 209137; and (e) the amino acid sequence of the mature huXAG-3 polypeptide having the amino acid sequence encoded by the cDNA clone contained in ATCC Deposit No. 209137.

The polypeptides of the present invention also include polypeptides having an amino acid sequence at least 95% identical, and more preferably at least 96%, 97%, 98% or 99% identical to the huXAG-1, huXAG-2 or huXAG-3 polypeptides described above.

An additional embodiment of this aspect of the invention relates to a peptide or polypeptide which has the amino acid sequence of an epitope-bearing portion of a huXAG-1, huXAG-2 or huXAG-3 polypeptide having an amino acid sequence described in (a), (b), (c), (d), or (e), above. Peptides or polypeptides having the amino acid sequence of an epitope-bearing portion of a huXAG-1, huXAG-2 or huXAG-3 polypeptide of the invention include portions of such polypeptides with at least six or seven, preferably at least nine, and more preferably at least about 30 amino acids to about 50 amino acids. It is understood that epitope-bearing polypeptides of any length up to and including the entire amino acid sequence of a polypeptide of the invention described above also are included in the invention. In another embodiment, the invention provides an isolated antibody that binds specifically to a huXAG-1, huXAG-2 or huXAG-3 polypeptide having an amino acid sequence described in (a), (b), (c), (d), or (e) above.

The invention further provides methods for isolating antibodies that bind specifically to a huXAG-1, huXAG-2 or huXAG-3 polypeptide having an amino acid sequence as described herein. Such antibodies are useful diagnostically or therapeutically as describe below.

The present invention also provides a screening method for identifying compounds capable of enhancing or inhibiting a cellular response induced by huXAG-1, huXAG-2 or huXAG-3 protein which involves contacting cells which express huXAG-1, huXAG-2 or huXAG-3 protein with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

A method for detecting and monitoring human colorectal carcinoma is based upon the discovery of the gene encoding huXAG-1. This protein was found to be expressed in cells derived from a human colon carcinoma, but not in other human tissues. In a first embodiment the method measures the level of huXAG-1 mRNA expression in a biological sample, preferably a tissue biopsy, and compares the measurement to a standard value. Levels of mRNA expression may be assayed by a variety of well-known methods, including Northern blot analysis, S1 nuclease mapping and polymerase chain reaction (PCR).

In a second embodiment, the method for detecting and monitoring human colorectal carcinoma includes contacting a biological sample with an antibody or portion thereof which reacts with huXAG-1, an analog, or portion thereof, and observing if the antibody reacts with the sample. The biological sample may be whole blood, serum, ascites fluid, a tissue biopsy, a tumor, a tissue culture, or a histological preparation thereof. The antibody may be raised to huXAG-1 polypeptide, or to analogs or antigenic portions thereof. More specifically, this antibody may be a polyclonal or monoclonal antibody, or analog or portion thereof, which preferably does not cross-react with CEA, NCA, CA 19.9, alpha-1-acid glycoprotein, or with the blood group substances A, B, and H. An immunoassay may be utilized to observe the extent of reaction between the receptor and the sample.

A detection method is also contemplated which enables the diagnosis and identification of a tumor cell in a biological sample from a patient. In this method the sample is subjected to at least one of a plurality of tests, each of which is specific for a particular tumor marker. The test may be any type of assay, preferably an immunoassay which employs an antibody specific for a tumor marker. The tests may be carried out sequentially until one of them indicates the presence of a particular marker.

Further, a kit for screening a patient for colorectal carcinoma is contemplated which contains a plurality of different antibodies specific for tumor markers. These antibodies may include those reacting with one of the following markers: huXAG-1; CEA; NCA; CA 19.9; and alpha-1-acid glycoprotein.

A method for diagnosis of diseases related to altered levels of huXAG-1, huXAG-2 or huXAG-3 gene expression is also provided.

Also provided are methods for identifying receptors of huXAG-1, huXAG-2 or huXAG-3.

An additional aspect of the invention is related to a method for treating an individual in need of an increased level of huXAG-1, huXAG-2 or huXAG-3 activity in the body comprising administering to such an individual a composition comprising a therapeutically effective amount of an isolated huXAG-1, huXAG-2, or huXAG-3 polypeptide of the invention or an agonist thereof.

A still further aspect of the invention is related to a method for treating an individual in need of a decreased level of huXAG-1, huXAG-2, or huXAG-3 activity in the body comprising administering to such an individual a composition comprising a therapeutically effective amount of an huXAG-1, huXAG-2, or huXAG-3 antagonist. Preferred antagonists for use in the present invention are huXAG-1-, huXAG-2-, or huXAG-3-specific antibodies.

BRIEF DESCRIPTION OF THE FIGURES

FIG. 1 shows the nucleotide (SEQ ID NO:1) and deduced amino acid (SEQ ID NO:2) sequences of huXAG-1. The protein has a leader sequence of about 20 amino acid residues (underlined) and a deduced molecular weight of about 20 kDa. The predicted amino acid sequence of the mature huXAG-1 protein is also shown.

FIGS. 2A-B show the nucleotide (SEQ ID NO:3) and deduced amino acid (SEQ ID NO:4) sequences of huXAG-2. The protein has a leader sequence of about 23 amino acid residues (underlined). The predicted amino acid sequence of the mature huXAG-2 protein is also shown.

FIGS. 3A-B show the nucleotide (SEQ ID NO:5) and deduced amino acid (SEQ ID NO:6) sequences of huXAG-3. The protein has a leader sequence of about 23 amino acid residues (underlined). The predicted amino acid sequence of the mature huXAG-3 protein is also shown.

FIGS. 4A-B show the regions of similarity between the amino acid sequences of the huXAG-1 (SEQ ID NO:2), huXAG-2 (SEQ ID NO:4), and huXAG-3 (SEQ ID NO:6) proteins and the *Xenopus laevis* XAG protein (SEQ ID NO:7). The consensus sequence is shown (SEQ ID NO:8).

DETAILED DESCRIPTION OF THE INVENTION

Figure 5:
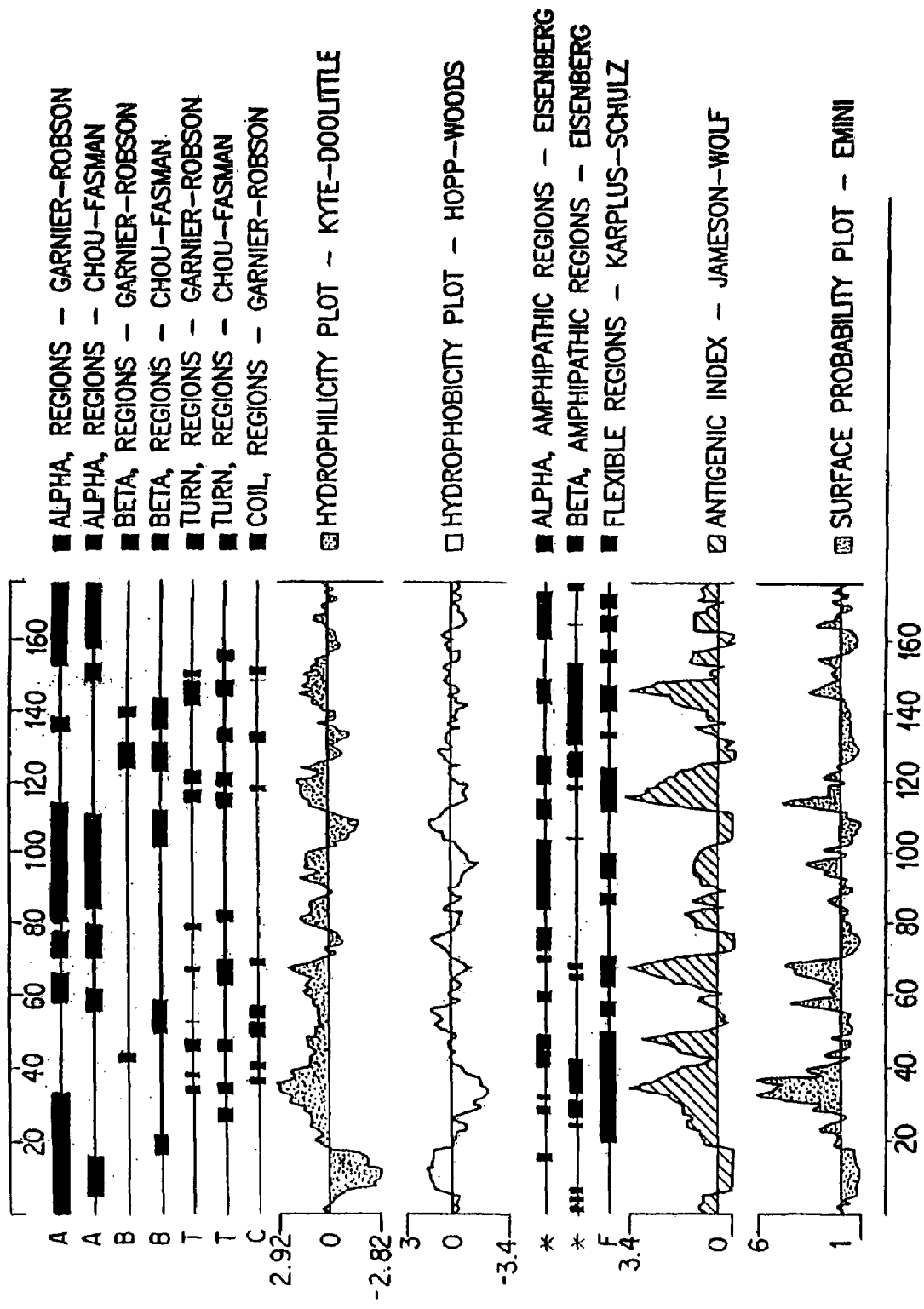
FIG. 5 shows an analysis of the huXAG-1 amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 20 to about 43, about 44 to about 52, about 61 to about 72, about 90 to about 103, about 113 to about 125, and about 138 to about 150 in FIG. 1 correspond to the shown highly antigenic regions of the huXAG-1 protein. These highly antigenic fragments in FIG. 1 correspond to the following fragments, respectively, in SEQ ID NO:2: amino acid residues about −1 to about 23, about 24 to about 32, about 41 to about 52, about 70 to about 83, about 93 to about 105, and about 118 to about 130.
Figure 6:
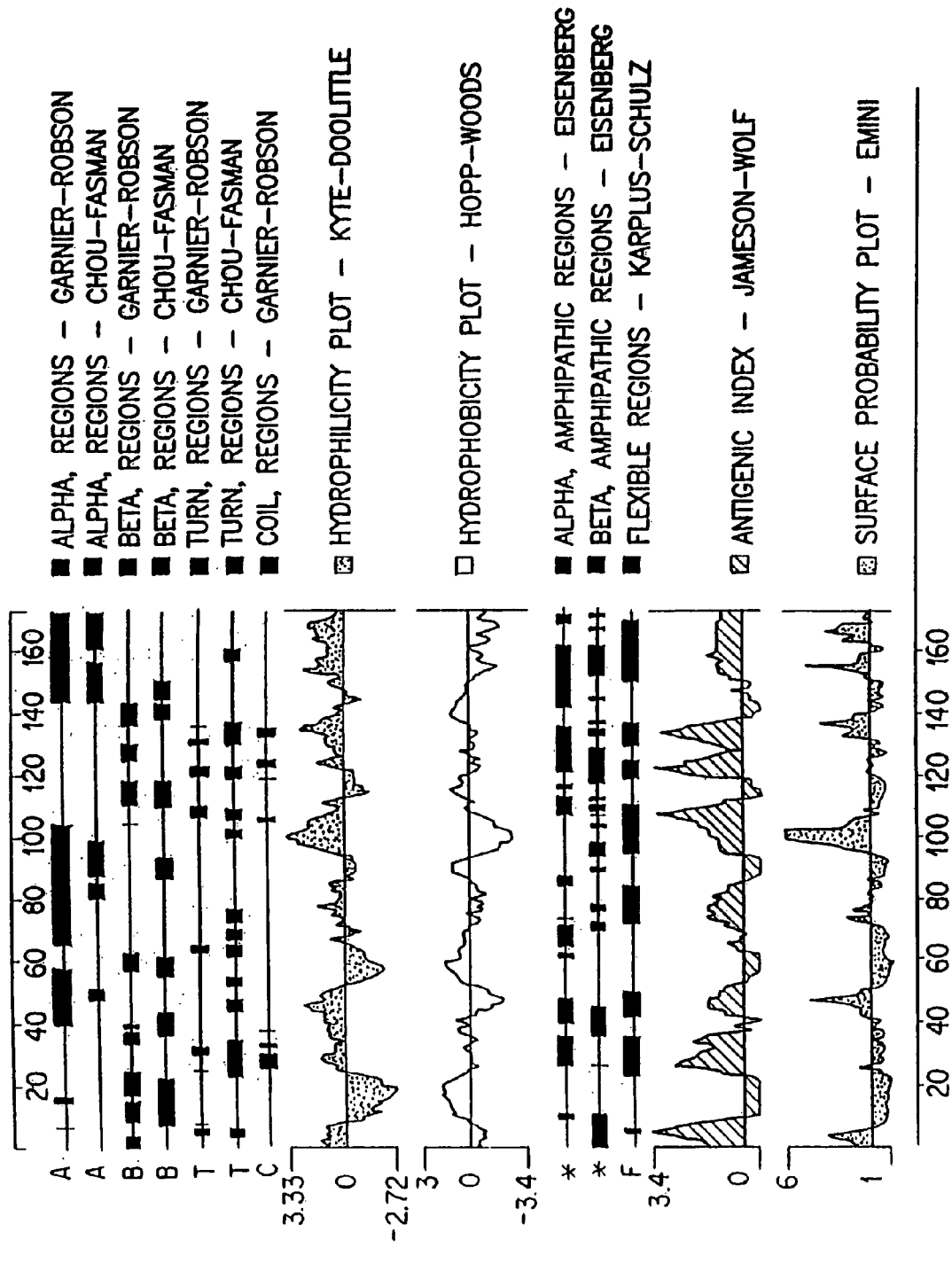
FIG. 6 shows an analysis of the huXAG-2 amino acid sequence, as described above for FIG. 5. In the "Antigenic Index—Jameson-Wolf" graph, amino acid residues about 23 to about 38, about 43 to about 53, about 94 to about 112, and about 120 to about 138 in FIG. 2 correspond to the shown highly antigenic regions of the huXAG-2 protein. These highly antigenic fragments in FIG. 2 correspond to the following fragments, respectively, in SEQ ID NO:4: amino acid residues about −1 to about 15, about 20 to about 30, about 71 to about 89, and about 97 to about 115.
Figure 7:
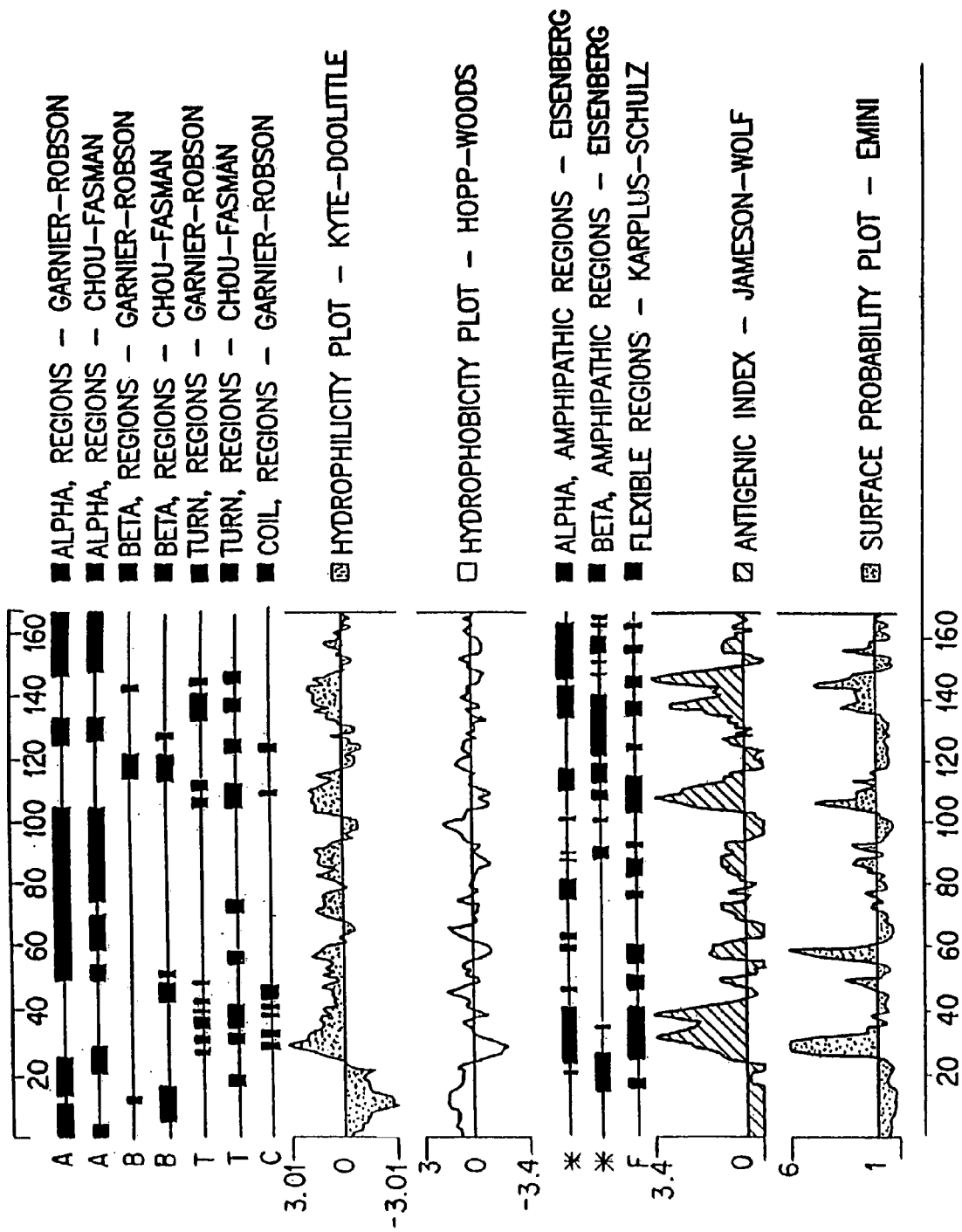
FIG. 7 shows an analysis of the huXAG-3 amino acid sequence, as described above for FIG. 5. In the "Antigenic Index—Jameson-Wolf" graph, amino acid residues about 25 to about 44, about 104 to about 155; and about 132 to about 150 in FIG. 3 correspond to the shown highly antigenic regions of the huXAG-3 protein. These highly antigenic fragments in FIG. 3 correspond to the following fragments, respectively, in SEQ ID NO:6: amino acid residues about 2 to about 21; about 81 to about 92, and about 109 to about 127.

The present inventors have identified a novel family of human growth factors, consisting of three members: huXAG-1, huXAG-2 and huXAG-3. These proteins share homology with the XAG protein of *Xenopus laevis*, which is involved in embryogenesis and is expressed in adult tissue. Overexpression of growth factors can lead to disease states, such as cancer. Underexpression of growth factors can also be detrimental, for example, in damaged tissue.

The present invention provides isolated nucleic acid molecules comprising a polynucleotide encoding a huXAG-1 polypeptide having the amino acid sequence shown in SEQ ID NO:2, which was determined by sequencing a cloned cDNA. The nucleotide sequence shown in SEQ ID NO:1 was obtained by sequencing a cDNA clone, which was deposited on Jun. 27, 1996 at the American Type Culture Collection, Patent Depository, 10801 University Boulevard, Manassas, Va. 20110-2209, and given accession number 97641. The deposited clone is inserted in the pBluescript SK(−) plasmid (Stratagene, LaJolla, Calif.) using the BamHI and Asp718I restriction endonuclease cleavage sites.

The present invention also provides isolated nucleic acid molecules comprising a polynucleotide encoding a huXAG-2 polypeptide having the amino acid sequence shown in SEQ ID NO:4, which was determined by sequencing a cloned cDNA. The nucleotide sequence shown in SEQ ID NO:3 was obtained by sequencing a cDNA clone, which was deposited on Jun. 27, 1997 at the American Type Culture Collection, Patent Depository, 10801 University Boulevard, Manassas, Va. 20110-2209, and given accession number 209134. The deposited clone is inserted in the pBluescript SK(−) plasmid (Stratagene, LaJolla, Calif.) using the BclI and Asp718I restriction endonuclease cleavage sites.

The present invention also provides isolated nucleic acid molecules comprising a polynucleotide encoding a huXAG-3 polypeptide having the amino acid sequence shown in SEQ ID NO:6, which was determined by sequencing a cloned cDNA. The nucleotide sequence shown in SEQ ID NO:5 was obtained by sequencing a cDNA clone, which was deposited on Jul. 3, 1997 at the American Type Culture Collection, Patent Depository, 10801 University Boulevard, Manassas, Va. 20110-2209, and given accession number 209137. The deposited clone is inserted in the pBluescript SK(−) plasmid (Stratagene, LaJolla, Calif.) using the BamHI and Asp718I restriction endonuclease cleavage sites.

The huXAG-1, huXAG-2 and huXAG-3 proteins of the present invention share sequence homology with the XAG protein of *Xenopus laevis* (FIG. 4) (SEQ ID NO:7).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Using the information provided herein, such as the nucleotide sequence in SEQ ID NO:1, SEQ ID NO:3, or SEQ ID NO:5, a nucleic acid molecule of the present invention encoding a huXAG-1, huXAG-2 or huXAG-3 polypeptide may be obtained using standard cloning and screening procedures, such as those for cloning cDNAs using mRNA as starting material. Illustrative of the invention, the nucleic acid molecule described in SEQ ID NO:1 was discovered in a cDNA library derived from human colon cancer tissue. No corresponding gene sequence was found when a cDNA library that was derived from normal colon tissue was screened. The determined nucleotide sequence of the huXAG-1 cDNA of SEQ ID NO:1 contains an open reading frame encoding a protein of 175 amino acid residues, with an initiation codon at positions 71-73 of the nucleotide sequence in SEQ ID NO:1, a predicted leader sequence of about 20 amino acid residues, and a deduced molecular weight of about 20 kDa. The amino acid sequence of the predicted mature huXAG-1 is shown in SEQ ID NO:2 from amino acid residue 1 to residue 155.

The nucleic acid molecule described in SEQ ID NO:3 was discovered in a cDNA library derived from human microvascular endothelial cells. The determined nucleotide sequence of the huXAG-2 cDNA of SEQ ID NO:3 contains an open reading frame encoding a protein of 172 amino acid residues, with an initiation codon at positions 88-90 of the nucleotide sequence in SEQ ID NO:3, and a predicted leader sequence of about 23 amino acid residues. The amino acid sequence of the predicted mature huXAG-3 is shown in SEQ ID NO:4 from amino acid residue 1 to residue 149.

The nucleic acid molecule described in SEQ ID NO:5 was discovered in a cDNA library derived from human small intestine. The determined nucleotide sequence of the huXAG-3 cDNA of SEQ ID NO:5 contains an open reading frame encoding a protein of 166 amino acid residues, with an initiation codon at positions 49-51 of the nucleotide sequence in SEQ ID NO:5, and a predicted leader sequence of about 23 amino acid residues. The amino acid sequence of the predicted mature huXAG-3 is shown in SEQ ID NO:6 from amino acid residue 1 to residue 143.

As indicated, the present invention also provides the mature form(s) of the huXAG-1, huXAG-2 and huXAG-3 proteins of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature huXAG-1, huXAG-2 and huXAG-3 polypeptides having the amino acid sequence encoded by the corresponding cDNA clone contained in ATCC Deposit No. 97641 and shown in SEQ ID NO:2; encoded by the cDNA clone in ATCC Deposit No. 209134 and as shown in SEQ ID NO:4; or encoded by the cDNA clone in ATCC Deposit No. 209137 and shown in SEQ ID NO:6, respectively. By the mature huXAG-1, huXAG-2 or huXAG-3 proteins having the amino acid sequence encoded by the cDNA clone contained in the host identified as ATCC Deposit No. 97641, ATCC Deposit No. 209134, or ATCC Deposit No. 209137, is meant the mature form(s) of the huXAG-1, huXAG-2 or huXAG-3 protein produced by expression in a mammalian cell (e.g., COS cells, as described below) of the complete open reading frame encoded by the human DNA sequence of the clone contained in the vector in the deposited host. As indicated below, the mature huXAG-1, huXAG-2 or huXAG-3 having the amino acid sequence encoded by the cDNA clone contained in ATCC Deposit No. 97641, ATCC Deposit No. 209134, or ATCC Deposit No. 209137 may or may not differ from the predicted "mature" huXAG-1, huXAG-2 or huXAG-3 protein shown in SEQ ID NO:2 (amino acids from about 1 to about 155), SEQ ID NO:4 (amino acids from about 1 to about 149), or SEQ ID NO:6 (amino acids from about 1 to about 143), respectively, depending on the accuracy of the predicted cleavage site based on computer analysis.

Methods for predicting whether a protein has a secretory leader as well as the cleavage point for that leader sequence are available because it is known that much of the cleavage specificity for a secretory protein resides in certain amino acid residues within the signal sequence and the N-terminus of the mature protein, particularly residues immediately surrounding the cleavage site. For instance, the method of McGeoch (*Virus Res.* 3:271-286 (1985)) uses the information from a short N-terminal charged region and a subsequent uncharged region of the complete (uncleaved) protein. The method of von Heinje (*Nucleic Acids Res.* 14:4683-4690 (1986)) uses the information from the residues surrounding the cleavage site, typically residues −13 to +2 where +1 indicates the amino acid terminus of the mature protein. The accuracy of predicting the cleavage points of known mammalian secretory proteins for each of these methods is in the range of 75-80%. von Heinje, supra. However, the two methods do not always produce the same predicted cleavage point(s) for a given protein.

The leader sequence for the huXAG-1 protein is predicted to consist of amino acid residues −20 to −1 in SEQ ID NO:2, while the predicted mature huXAG-1 protein consists of residues 1-155; the leader sequence for the huXAG-2 protein is predicted to consist of amino acid residues −23 to −1 in SEQ ID NO:4, while the predicted mature huXAG-2 protein consists of residues 1-149; and the leader sequence for the huXAG-3 protein is predicted to consist of amino acid residues −23 to −1 in SEQ ID NO:6, while the predicted mature huXAG-3 protein consists of residues 1-143.

As one of ordinary skill would appreciate, due to the possibilities of sequencing errors, as well as the variability of cleavage sites for leaders in different known proteins, the predicted huXAG-1 polypeptide encoded by the deposited cDNA comprises about 175 amino acids, but may be anywhere in the range of 165-185 amino acids; and the predicted leader sequence of huXAG-1 is about 20 amino acids, but may be anywhere in the range of about 15 to about 25 amino acids. The predicted huXAG-2 polypeptide encoded by the deposited cDNA comprises about 172 amino acids, but may be anywhere in the range of 167-177 amino acids; and the predicted leader sequence of huXAG-2 is about 23 amino acids, but may be anywhere in the range of about 18 to about 28 amino acids. The predicted huXAG-3 polypeptide encoded by the deposited cDNA comprises about 166 amino acids, but may be anywhere in the range of 161-171 amino acids; and the predicted leader sequence of huXAG-3 is about 23 amino acids, but may be anywhere in the range of about 18 to about 28 amino acids.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 71-73 of the nucleotide sequence shown in SEQ ID NO:1; DNA molecules comprising the coding sequence for the mature huXAG-1 protein shown in FIG. 1 (last 155 amino acids) (SEQ ID NO:2); DNA molecules comprising an open reading frame (ORF) with an initiation codon at positions 88-90 of the nucleotide sequence shown in SEQ ID NO:3; DNA molecules comprising the coding sequence for the mature huXAG-2 protein shown in FIG. 2 (last 149 amino acids) (SEQ ID NO:4); DNA molecules comprising an open reading frame (ORF) with an initiation codon at positions 49-51 of the nucleotide sequence shown in SEQ ID NO:5; DNA molecules comprising the coding sequence for the mature huXAG-3 protein shown in FIG. 3 (last 143 amino acids) (SEQ ID NO:6); and DNA molecules which comprise a sequence substantially different from those described above but which, due to the degeneracy of the genetic code, still encode the huXAG-1, huXAG-2 or huXAG-3 protein. Of course, the genetic code is well known in the art. Thus, it would be routine for one skilled in the art to generate the degenerate variants described above.

In another aspect, the invention provides isolated nucleic acid molecules encoding the huXAG-1 polypeptide having an amino acid sequence encoded by the cDNA clone contained in the plasmid deposited as ATCC Deposit No. 97641 on Jun. 27, 1996; isolated nucleic acid molecules encoding the huXAG-2 polypeptide having an amino acid sequence encoded by the cDNA clone contained in the plasmid deposited as ATCC Deposit No. 209134 on Jun. 27, 1997; and isolated nucleic acid molecules encoding the huXAG-3 polypeptide having an amino acid sequence encoded by the cDNA clone contained in the plasmid deposited as ATCC Deposit No. 209137 on Jul. 3, 1997. In a further embodiment, nucleic acid molecules are provided encoding the mature huXAG-1, huXAG-2 or huXAG-3 polypeptide or the full-length huXAG-1, huXAG-2 or huXAG-3 polypeptide lacking the N-terminal methionine.

The invention further provides an isolated nucleic acid molecule having the nucleotide sequence shown in SEQ ID NO:1, SEQ ID NO:3 or SEQ ID NO:5 or the nucleotide sequence of the huXAG-1, huXAG-2 or huXAG-3 cDNA contained in the above-described deposited clones, or a nucleic acid molecule having a sequence complementary to one of the above sequences. Such isolated molecules, particularly DNA molecules, are useful as probes for gene mapping, by in situ hybridization with chromosomes, and for detecting expression of the huXAG-1, huXAG-2 or huXAG-3 genes in human tissue, for instance, by Northern blot analysis.

The present invention is further directed to fragments of the isolated nucleic acid molecules described herein. By a fragment of an isolated nucleic acid molecule having the nucleotide sequence of the deposited cDNAs or the nucleotide sequence shown in SEQ ID NO:1, SEQ ID NO:3 or SEQ ID NO:5 is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 100, 150, 200, 250, 300, 350, 400, or 450 nt in length are also useful according to the present invention as are fragments corresponding to most, if not all, of the nucleotide sequence of the deposited cDNAs or as shown in SEQ ID NO:1, SEQ ID NO:3 or SEQ ID NO:5. By a fragment at least 20 nt in length, for example, is intended fragments which include 20 or more contiguous bases from the nucleotide sequence of the deposited cDNA or the nucleotide sequence as shown in SEQ ID NO:1, SEQ ID NO:3 or SEQ ID NO:5. Since the genes have been deposited and the nucleotide sequences shown in SEQ ID NO:1, SEQ ID NO:3 and SEQ ID NO:5 are provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding epitope-bearing portions of the huXAG-1, huXAG-2 and huXAG-3 proteins.

In particular, such nucleic acid fragments of the present invention include nucleic acid molecules encoding: a polypeptide comprising amino acid residues from about −1 to about 23 in SEQ ID NO:2; a polypeptide comprising amino acid residues from about 24 to about 32 in SEQ ID NO:2; a polypeptide comprising amino acid residues from about 41 to about 52 in SEQ ID NO:2; a polypeptide comprising amino acid residues from about 70 to about 83 in SEQ ID NO:2; a polypeptide comprising amino acid residues from about 93 to about 105 in SEQ ID NO:2; a polypeptide comprising amino acid residues from about 118 to about 130 in SEQ ID NO:2; a polypeptide comprising amino acid residues from about −1 to about 15 in SEQ ID NO:4; a polypeptide comprising amino acid residues from about 20 to about 30 in SEQ ID NO:4; a polypeptide comprising amino acid residues from about 71 to about 89 in SEQ ID NO:4; a polypeptide comprising amino acid residues from about 97 to about 115 in SEQ ID NO:4; a polypeptide comprising amino acid residues from about 2 to about 21 in SEQ ID NO:6; a polypeptide comprising amino acid residues from about 81 to about 92 in SEQ ID NO:6; and a polypeptide comprising amino acid residues from about 109 to about 127 in SEQ ID NO:6. The inventors have determined that the above polypeptide fragments are antigenic regions of the huXAG-1, huXAG-2 and huXAG-3 proteins. Methods for determining other such epitope-bearing portions of the huXAG-1, huXAG-2 and huXAG-3 proteins are described in detail below.

In addition, the present inventors have identified the following cDNA clones related to portions of SEQ ID NO:1: HE2DM19R (SEQ ID NO:9), HPFDA02R (SEQ ID NO:10), HBGDA10R (SEQ ID NO:11), HBGDA22R (SEQ ID NO:12), HBGDA34R (SEQ ID NO:13), HBGDA58R (SEQ ID NO:14), and HBGDA46R (SEQ ID NO:15).

The following public ESTs, which relate to portions of SEQ ID NO:1, have also been identified: GenBank Accession No. AA244356 (SEQ ID NO:35); GenBank Accession No. T86663 (SEQ ID NO:36); GenBank Accession No. AA055880 (SEQ ID NO:37); GenBank Accession No. T24475 (SEQ ID NO:38); and GenBank Accession No. T24892 (SEQ ID NO:39).

The present inventors have also identified the following cDNA clones related to portions of SEQ ID NO:3: HJPAJ39R (SEQ ID NO:16), HPASG11R (SEQ ID NO:17), HOSBP40R (SEQ ID NO:18), HTEAK67R (SEQ ID NO:19), HLQBB65R (SEQ ID NO:20), HLQBB77R (SEQ ID NO:21), and HJPAC37R (SEQ ID NO:22). A number of public ESTs related to portions of SEQ ID NO:3 are listed in GenBank.

The following public ESTs, related to portions of SEQ ID NO:5, have been identified: GenBank Accession No. T94990 (SEQ ID NO:40); and GenBank Accession No. T94936 (SEQ ID NO:41).

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 97641 or ATCC Deposit No. 209134 or ATCC Deposit No. 209137. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70 nt of the reference polynucleotide. These are useful as diagnostic probes and primers as discussed above and in more detail below.

Of course, polynucleotides hybridizing to a larger portion of the reference polynucleotide (e.g., the deposited cDNA clones), for instance, a portion 50-500, 100, 150, 200, 250, 300, 350, 400, or 450 nt in length, or even to the entire length of the reference polynucleotide, are also useful as probes according to the present invention, as are polynucleotides corresponding to most, if not all, of the nucleotide sequence of the deposited cDNAs or the nucleotide sequence as shown in SEQ ID NO:1, SEQ ID NO:3 or SEQ ID NO:5. By a portion of a polynucleotide of "at least 20 nt in length," for example, is intended 20 or more contiguous nucleotides from the nucleotide sequence of the reference polynucleotide (e.g., the deposited cDNAs or the nucleotide sequence as shown in SEQ ID NO:1, SEQ ID NO:3 or SEQ ID NO:5). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since huXAG-1, huXAG-2 and huXAG-3 cDNA clones have been deposited and their determined nucleotide sequences are provided in SEQ ID NO:1, SEQ ID NO:3 and SEQ ID NO:5, respectively, generating polynucleotides which hybridize to a portion of the huXAG-1, huXAG-2 or huXAG-3 cDNA molecules would be routine to the skilled artisan. For example, restriction endonuclease cleavage or shearing by sonication of the huXAG-1, huXAG-2 or huXAG-3 cDNA clones could easily be used to generate DNA portions of various sizes which are polynucleotides that hybridize to a portion of the huXAG-1, huXAG-2 or huXAG-3 cDNA molecules. Alternatively, the hybridizing polynucleotides of the present invention could be generated synthetically according to known techniques. Of course, a polynucleotide which hybridizes only to a poly A sequence (such as the 3' terminal poly(A) tract of the huXAG-1, huXAG-2 or huXAG-3 cDNAs shown in SEQ ID NO:1, SEQ ID NO:3 and SEQ ID NO:5, respectively), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a huXAG-1, huXAG-2 or huXAG-3 polypeptide may include, but are not limited to those encoding the amino acid sequence of the mature polypeptide, by itself, the coding sequence for the mature polypeptide and additional sequences, such as those encoding the about 20 amino acid leader or secretory sequence of huXAG-1, or the about 23 amino acid leader or secretory sequence of huXAG-2, or the about 23 amino acid leader or secretory sequence of huXAG-3, such as a pre-, or pro- or prepro-protein sequence; the coding sequence of the mature polypeptides, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the huXAG-1, huXAG-2 or huXAG-3 fused to Fc at the N- or C-terminus.

The present invention further relates to variants of the nucleic acid molecules of the present invention, which encode portions, analogs or derivatives of the huXAG-1, huXAG-2 or huXAG-3 proteins. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the huXAG-1, huXAG-2 or huXAG-3 proteins or portions thereof. Also especially preferred in this regard are conservative substitutions. Most highly preferred are nucleic acid molecules encoding the mature proteins having the amino acid sequence shown in SEQ ID NO:2, SEQ ID NO:4 or SEQ ID NO:6; or the mature huXAG-1, huXAG-2 or huXAG-3 amino acid sequences encoded by the deposited cDNA clones.

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2, SEQ ID NO:4 or SEQ ID NO:6; (b) a nucleotide sequence encoding the polypeptide having the amino acid sequence in SEQ ID NO:2, SEQ ID NO:4 or SEQ ID NO:6 but lacking the N-terminal methionine; (c) a nucleotide sequence encoding the polypeptide having the amino acid sequence at positions from about 1 to about 155 in SEQ ID NO:2; or from about 1 to about 149 in SEQ ID NO:4; or from about 1 to about 143 in SEQ ID NO:6; (d) a nucleotide sequence encoding the polypeptide having the amino acid sequence encoded by the cDNA clone contained in ATCC Deposit No. 97641, or in ATCC Deposit No. 209134, or in ATCC Deposit No. 209137; (e) a nucleotide sequence encoding the mature huXAG-1, huXAG-2 or huXAG-3 polypeptide having the amino acid sequence encoded by the cDNA clone contained in ATCC Deposit No. 97641, ATCC Deposit No. 209134 or ATCC Deposit No. 209137, respectively; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a huXAG-1, huXAG-2 or huXAG-3 polypeptide is intended that the nucleotide sequence of the polynucleotide is identical to the reference sequence except that the polynucleotide sequence may include up to five point mutations per each 100 nucleotides of the reference nucleotide sequence encoding the huXAG-1, huXAG-2 or huXAG-3 polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1, SEQ ID NO:3 or SEQ ID NO:5 or to the nucleotides sequence of the deposited cDNA clones can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in SEQ ID NO:1, SEQ ID NO:3 or SEQ ID NO:5 or to the nucleic acid sequence of the deposited cDNAs, irrespective of whether they encode a polypeptide having huXAG-1, huXAG-2 or huXAG-3 activity. This is because even where a particular nucleic acid molecule does not encode a polypeptide having huXAG-1, huXAG-2 or huXAG-3 activity, one of skill in the art would still know how to use the nucleic acid molecule, for instance, as a hybridization probe or a polymerase chain reaction (PCR) primer. Uses of the nucleic acid molecules of the present invention that do not encode a polypeptide having huXAG-1, huXAG-2 or huXAG-3 activity include, inter alia, (1) isolating the huXAG-1, huXAG-2 or huXAG-3 gene or allelic variants thereof in a cDNA library; (2) in situ hybridization (e.g., "FISH") to metaphase chromosomal spreads to provide precise chromosomal location of the huXAG-1, huXAG-2 or huXAG-3 gene, as described in Verma et al., *Human Chromosomes: A Manual of Basic Techniques*, Pergamon Press, New York (1988); and (3) Northern Blot analysis for detecting huXAG-1, huXAG-2 or huXAG-3 mRNA expression in specific tissues.

Preferred, however, are nucleic acid molecules having sequences at least 95%, 96%, 97%, 98% or 99% identical to the nucleic acid sequence shown in SEQ ID NO:1, SEQ ID NO:3 or SEQ ID NO:5 or to the nucleic acid sequence of the deposited cDNAs which do, in fact, encode a polypeptide having huXAG-1, huXAG-2 or huXAG-3 protein activity. By "a polypeptide having huXAG-1, huXAG-2 or huXAG-3 activity" is intended polypeptides exhibiting activity similar, but not necessarily identical, to an activity of the huXAG-1, huXAG-2 or huXAG-3 protein of the invention (either the full-length protein or, preferably, the mature protein), as measured in a particular biological assay. To measure huXAG-1, huXAG-2 or huXAG-3 activity, a cell proliferation assay can be used. For huXAG-1, cancerous colon cells can be used. For huXAG-2, microvascular endothelial cells can be used, as well as other cells which are responsive to huXAG-2. For huXAG-3, colon cells can be used, as well as other cells that are responsive to huXAG-3. There are several protocols to perform cell proliferation assays that are well known in the art. Typically, the incorporation of a nucleoside analog into newly synthesized DNA is employed to measure proliferation (active cell growth) in a population of cells. For example, bromodeoxyuridine (BrdU) can be employed as a DNA labeling reagent and Anti-BrdU mouse monoclonal antibody (clone BMC 9318 $IgG_1$) can be employed as a detection reagent. This antibody binds only to cells containing DNA which has incorporated bromodeoxyuridine. A number of detection methods can be used in conjunction with this assay including immunofluorescence, immunohistochemical, ELISA and colorimetric methods. Kits that include bromodeoxyuridine (BrdU) and Anti-BrdU mouse monoclonal antibody are commercially available from Boehringer Mannheim (Indianapolis, Ind.).

Thus, "a polypeptide having huXAG-1, huXAG-2 or huXAG-3 protein activity" includes polypeptides that exhibit huXAG-1, huXAG-2 or huXAG-3 activity, in an appropriate above-described assay. Although the degree of activity need not be identical to that of the huXAG-1, huXAG-2 or huXAG-3 protein, preferably, "a polypeptide having huXAG-1, huXAG-2 or huXAG-3 protein activity" will exhibit substantially similar activity as compared to the huXAG-1, huXAG-2 or huXAG-3 protein (i.e., the candidate polypeptide will exhibit greater activity or not more than about twenty-fold less and, preferably, not more than about ten-fold less activity relative to the reference huXAG-1, huXAG-2 or huXAG-3 protein).

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited cDNAs or the nucleic acid sequence shown in SEQ ID NO:1, SEQ ID NO:3 or SEQ ID NO:5 will encode a polypeptide "having huXAG-1, huXAG-2 or huXAG-3 protein activity." In fact, since degenerate variants of these nucleotide sequences all encode the same polypeptide, this will be clear to the skilled artisan even without performing the above described comparison assays. It will be further recognized in the art that, for such nucleic acid molecules that are not degenerate variants, a reasonable number will also encode a polypeptide having huXAG-1, huXAG-2 or huXAG-3 protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," Science 247:1306-1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality. As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein.

Vectors and Host Cells

The present invention also relates to vectors which include the isolated DNA molecules of the present invention, host cells which are genetically engineered with the recombinant vectors, and the production of huXAG-1, huXAG-2 or huXAG-3 polypeptides or fragments thereof by recombinant techniques.

Recombinant constructs may be introduced into host cells using well known techniques such as infection, transduction, transfection, transvection, electroporation and transformation. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5- has been fused with Fc portions for the purpose of high-throughput screening assays to identify antagonists of hIL-5. See, D. Bennett et al., *Journal of Molecular Recognition*, Vol. 8:52-58 (1995) and K. Johanson et al., *The Journal of Biological Chemistry*, Vol. 270, No. 16:9459-9471 (1995).

The huXAG-1, huXAG-2 or huXAG-3 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

huXAG-1, huXAG-2 and huXAG-3 Polypeptides and Fragments

The invention further provides an isolated huXAG-1 polypeptide having the amino acid sequence encoded by the cDNA in ATCC Deposit No. 97641, or the amino acid sequence in SEQ ID NO:2, or a peptide or polypeptide comprising a portion of the above polypeptides. The invention also provides an isolated huXAG-2 polypeptide having the amino acid sequence encoded by the cDNA in ATCC Deposit No. 209134, or the amino acid sequence in SEQ ID NO:4, or a peptide or polypeptide comprising a portion thereof. The invention further provides an isolated huXAG-3 polypeptide having the amino acid sequence encoded by the cDNA in ATCC Deposit No. 209137, or the amino acid sequence in SEQ ID NO:6, or a peptide or polypeptide comprising a portion thereof. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the huXAG-1, huXAG-2 and huXAG-3 polypeptides can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of huXAG-1, huXAG-2 and huXAG-3 polypeptides which show substantial huXAG-1, huXAG-2 or huXAG-3 polypeptide activity or which include regions of huXAG-1, huXAG-2 or huXAG-3 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306-1310 (1990).

Thus, the fragment, derivative or analog of a polypeptide of SEQ ID NO:2, SEQ ID NO:4, or SEQ ID NO:6 or that encoded by the deposited cDNAs, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of a huXAG-1, huXAG-2 or huXAG-3 protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331-340 (1967); Robbins et al., *Diabetes* 36:838-845 (1987); Cleland et al. *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993) describes certain mutations resulting in selective binding of TNF-α to only one of the two known types of TNF receptors. Thus, the huXAG-1, huXAG-2 and huXAG-3 of the present invention may include one or more amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| Hydrophobic | Tryptophan |
| Polar | Tyrosine |
| Basic | Leucine |
| Acidic | Isoleucine |
| Small | Valine |
| | Glutamine |
| | Asparagine |
| | Arginine |
| | Lysine |
| | Histidine |
| | Aspartic Acid |
| | Glutamic Acid |
| | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given hu-XAG-1, huXAG-2, or huXAG-3 polypeptide will not be more than 50, 40, 30, 20, 10, 5, or 3.

Amino acids in the huXAG-1, huXAG-2 and huXAG-3 proteins of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell or a native source. For example, a recombinantly produced version of the huXAG-1, huXAG-2 or huXAG-3 polypeptide can be substantially purified by the one-step method described in Smith and Johnson, Gene 67:31-40 (1988).

The polypeptides of the present invention include the polypeptide encoded by the deposited cDNAs including the leader; the mature polypeptide encoded by the deposited the cDNAs minus the leader (i.e., the mature protein); a polypeptide comprising amino acids about −20 to about 155 in SEQ ID NO:2; a polypeptide comprising amino acids about −19 to about 155 in SEQ ID NO:2; a polypeptide comprising amino acids about 1 to about 155 in SEQ ID NO:2; a polypeptide comprising amino acids about −23 to about 149 in SEQ ID NO:4; a polypeptide comprising amino acids about −22 to about 149 in SEQ ID NO:4; a polypeptide comprising amino acids about 1 to about 149 in SEQ ID NO:4; a polypeptide comprising amino acids about −23 to about 143 in SEQ ID NO:6; a polypeptide comprising amino acids about −22 to about 143 in SEQ ID NO:6; a polypeptide comprising amino acids about 1 to about 143 in SEQ ID NO:6 as well as polypeptides which at least 95% identical, and more preferably at least 96%, 97%, 98% or 99% identical to the polypeptide encoded by the deposited cDNAs, to the polypeptide of SEQ ID NO:2, SEQ ID NO:4 or SEQ ID NO:6 and also include portions of such polypeptides with at least 30 amino acids and more preferably at least 50 amino acids.

By a polypeptide having an amino acid sequence at least, for example, 95% "identical" to a reference amino acid sequence of a huXAG-1, huXAG-2 or huXAG-3 polypeptide is intended that the amino acid sequence of the polypeptide is identical to the reference sequence except that the polypeptide sequence may include up to five amino acid alterations per each 100 amino acids of the reference amino acid of the huXAG-1, huXAG-2 or huXAG-3 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2, SEQ ID NO:4 or SEQ ID NO:6 or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting huXAG-1, huXAG-2 or huXAG-3 protein expression as described below or as agonists and antagonists capable of enhancing or inhibiting huXAG-1, huXAG-2 or huXAG-3 protein function. Further, such polypeptides can be used in the yeast two-hybrid system to "capture" huXAG-1, huXAG-2 or huXAG-3 protein binding proteins which are also candidate agonist and antagonist according to the present invention. The yeast two hybrid system is described in Fields and Song, Nature 340:245-246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. Science 219:660-666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing.

The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson et al., Cell 37:767-778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

Non-limiting examples of antigenic polypeptides or peptides that can be used to generate huXAG-1-, huXAG-2 or hu-XAG-3-specific antibodies include: a polypeptide comprising amino acid residues from about −1 to about 23 in SEQ ID NO:2; a polypeptide comprising amino acid residues from about 24 to about 32 in SEQ ID NO:2; a polypeptide comprising amino acid residues from about 41 to about 52 in SEQ ID NO:2; a polypeptide comprising amino acid residues from about 70 to about 83 in SEQ ID NO:2; a polypeptide comprising amino acid residues from about 93 to about 105 in SEQ ID NO:2; a polypeptide comprising amino acid residues from about 118 to about 130 in SEQ ID NO:2; a polypeptide comprising amino acid residues from about −1 to about 15 in SEQ ID NO:4; a polypeptide comprising amino acid residues from about 20 to about 30 in SEQ ID NO:4; a polypeptide comprising amino acid residues from about 71 to about 89 in SEQ ID NO:4; a polypeptide comprising amino acid residues from about 97 to about 115 in SEQ ID NO:4; a polypeptide comprising amino acid residues from about 2 to about 21 in SEQ ID NO:6; a polypeptide comprising amino acid residues from about 81 to about 92 in SEQ ID NO:6; and a polypeptide comprising amino acid residues from about 109 to about 127 in SEQ ID NO:6. As indicated above, the inventors have determined that the above polypeptide fragments are antigenic regions of the huXAG-1, huXAG-2 and hu-XAG-3 proteins.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. Proc. Natl. Acad. Sci. USA 82:5131-5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously. Houghten et al., supra, at 5134.

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910-914; and Bittle, F. J. et al., J. Gen. Virol. 66:2347-2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. supra with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$-$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, huXAG-1, huXAG-2 and huXAG-3 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric huXAG-1, huXAG-2 or huXAG-3 protein or protein fragment alone (Fountoulakis et al., *J. Biochem* 270:3958-3964 (1995)).

Diagnostic and Therapeutic Applications of huXAG-1, huXAG-2 and huXAG-3

The present inventors have identified a novel family of human growth factors, consisting of three members: huXAG-1, huXAG-2 and huXAG-3. These proteins share homology with the XAG protein of *Xenopus laevis*, which is involved in embryogenesis and is expressed in adult tissue. Overexpression of growth factors can lead to disease states, such as cancer.

Underexpression of Growth Factors can Also be Detrimental, for Example, in Damaged Tissue.

Expression of huXAG-1 has been discovered in colon cancer tissue. However, no corresponding gene expression was found in normal colon tissue. Thus, the huXAG-1 gene of the present invention provides a molecular marker for colon cancer, including polypoisis and non-polypoisis cancer. huXAG-1 gene expression can be detected in colon tissue or bodily fluids (i.e., sera, plasma, urine, synovial fluid or spinal fluid) taken from an individual suspected of having colon cancer. Thus, the invention provides a diagnostic method useful during diagnosis of colon cancer, which involves measuring the expression level of the gene encoding the huXAG-1 protein in colon tissue or body fluid from a first individual and comparing the measured gene expression level with a standard huXAG-1 gene expression level taken from one or more individuals known not to have colon cancer whereby an increase in the gene expression level compared to the standard is indicative of colon cancer. As indicated, since huXAG-1 gene expression in normal colon tissue has not been detected, the standard expression level will be significantly lower than the expression level of huXAG-1 in an individual with colon cancer.

Where a tumor diagnosis has already been made according to conventional methods, the present invention is useful as a prognostic indicator, whereby patients exhibiting enhanced huXAG-1 gene expression will experience a worse clinical outcome relative to patients expressing the gene at a lower level.

The present invention also relates to a diagnostic assay for detecting altered levels of huXAG-2 or huXAG-3 protein in various tissues since an over-expression of the proteins compared to normal control tissue samples can detect the presence of a disease or susceptibility to a disease, for example, a tumor. Thus, the present invention provides a diagnostic method which involves measuring the expression level of the gene encoding huXAG-2 or huXAG-3 in tissue or body fluid taken from a first individual and comparing the measured gene expression level with a standard huXAG-2 or huXAG-3 gene expression level taken from one or more individuals known not to have the disease being diagnosed, whereby an increase in the gene expression level compared to the standard is indicative of disease.

By "assaying the expression level of the gene encoding the huXAG-1, huXAG-2 or huXAG-3 protein" is intended qualitatively or quantitatively measuring or estimating the level of the huXAG-1, huXAG-2, or huXAG-3 protein or the level of the mRNA encoding the huXAG-1, huXAG-2, or huXAG-3 protein in a first biological sample either directly (e.g., by determining or estimating absolute protein level or mRNA level) or relatively (e.g., by comparing to the huXAG-1, huXAG-2 or huXAG-3 protein level or mRNA level in a second biological sample).

Preferably, the huXAG-1, huXAG-2 or huXAG-3 protein level or mRNA level in the first biological sample is measured or estimated and compared to a standard huXAG-1, huXAG-2, or huXAG-3 protein level or mRNA level, the standard being taken from a second biological sample obtained from an individual not having the disease. As will be appreciated in the art, once a standard huXAG-1, huXAG-2, or huXAG-3 protein level or mRNA level is known, it can be used repeatedly as a standard for comparison.

By "biological sample" is intended any biological sample obtained from an individual, cell line, tissue culture, or other source which contains huXAG-1, huXAG-2 or huXAG-3 protein or mRNA. Biological samples include mammalian body fluids (such as sera, plasma, urine, synovial fluid and spinal fluid) which contain secreted mature huXAG-1, huXAG-2 or huXAG-3 protein, and tissue. Preferred tissue for huXAG-1 expression detection is colon tissue. Methods for obtaining tissue biopsies and body fluids from mammals are well known in the art. Where the biological sample is to include mRNA, a tissue biopsy is the preferred source.

The present invention is useful for detecting cancer in mammals. In one preferred embodiment, the invention is useful during diagnosis of the of colon cancer in mammals. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenol-chloroform method described in Chomczynski and Sacchi, *Anal. Biochem.* 162:

156-159 (1987). Levels of mRNA encoding the huXAG-1, huXAG-2 or huXAG-3 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303-312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. huXAG-1, huXAG-2 or huXAG-3 protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357-367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the huXAG-1, huXAG-2 or huXAG-3 protein). Northern blot analysis can be performed as described above.

Preferably, levels of mRNA encoding the huXAG-1, huXAG-2 or huXAG-3 protein are assayed using the RT-PCR method described in Makino et al., *Technique* 2:295-301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the huXAG-1, huXAG-2 or huXAG-3 protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying huXAG-1, huXAG-2 or huXAG-3 protein levels in a biological sample can occur using any art-known method.

Preferred for assaying huXAG-1, huXAG-2 or huXAG-3 protein levels in a biological sample are antibody-based techniques. For example, huXAG-1, huXAG-2 or huXAG-3 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of huXAG-1, huXAG-2 or huXAG-3 protein for Western-blot or dot/slot assay (Jalkanen, M., et al., *J. Cell. Biol.* 101:976-985 (1985); Jalkanen, M., et al., *J. Cell. Biol.* 105: 3087-3096 (1987)). In this technique, which is based on the use of cationic solid phases, quantitation of huXAG-1, huXAG-2 or huXAG-3 protein can be accomplished using isolated huXAG-1, huXAG-2 or huXAG-3 protein, respectively, as a standard. This technique can also be applied to body fluids. With these samples, a molar concentration of huXAG-1, huXAG-2 or huXAG-3 protein will aid to set standard values of huXAG-1, huXAG-2 or huXAG-3 protein content, respectively, for different body fluids, like serum, plasma, urine, spinal fluid, etc. The normal appearance of huXAG-1, huXAG-2 or huXAG-3 protein amounts can then be set using values from healthy individuals, which can be compared to those obtained from a test subject.

Other antibody-based methods useful for detecting huXAG-1, huXAG-2 or huXAG-3 protein gene expression include immunoassays, such as the enzyme linked immunosorbent assay (ELISA) and the radioimmunoassay (RIA). For example, huXAG-1, huXAG-2 or huXAG-3 protein-specific monoclonal antibodies can be used both as an immunoabsorbent and as an enzyme-labeled probe to detect and quantify the huXAG-1, huXAG-2 or huXAG-3 protein, respectively. The amount of huXAG-1, huXAG-2 or huXAG-3 protein present in the sample can be calculated by reference to the amount present in a standard preparation using a linear regression computer algorithm. Such an ELISA for detecting a tumor antigen is described in Iacobelli et al., *Breast Cancer Research and Treatment* 11:19-30 (1988). In another ELISA assay, two distinct specific monoclonal antibodies can be used to detect huXAG-1, huXAG-2 or huXAG-3 protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting huXAG-1, huXAG-2 or huXAG-3 protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^3$H), indium ($^{111}$In), and technetium ($^{99m}$Tc), and fluorescent labels, such as fluorescein and rhodamine, and biotin.

In addition to assaying huXAG-1, huXAG-2 or huXAG-3 protein levels in a biological sample obtained from an individual, huXAG-1, huXAG-2 or huXAG-3 protein can also be detected in vivo by imaging. Antibody labels or markers for in vivo imaging of huXAG-1, huXAG-2 or huXAG-3 protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A huXAG-1, huXAG-2 or huXAG-3 protein-specific antibody or antibody fragment which has been labeled with an appropriate detectable imaging moiety, such as a radioisotope (for example, $^{131}$I, $^{111}$In, $^{99m}$Tc), a radio-opaque substance, or a material detectable by nuclear magnetic resonance, is introduced (for example, parenterally, subcutaneously or intraperitoneally) into the mammal to be examined for cancer. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain huXAG-1, huXAG-2 or huXAG-3 protein, respectively. In vivo tumor imaging is described in S. W. Burchiel et al., "Immunopharmacokinetics of Radiolabelled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

A huXAG-1-, huXAG-2- or huXAG-3-protein specific antibody for use in the present invention can be raised against the intact huXAG-1, huXAG-2 or huXAG-3 protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to huXAG-1, huXAG-2 or huXAG-3 protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies of the present invention may be prepared by any of a variety of methods. For example, cells expressing the huXAG-1, huXAG-2 or huXAG-3 protein or an antigenic fragment thereof can be administered to an animal in order to induce the production of sera containing polyclonal antibodies. In a preferred method, a preparation of huXAG-1, huXAG-2 or huXAG-3 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or huXAG-1, huXAG-2 or huXAG-3 protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., (1981) pp. 563-681). In general, such procedures involve immunizing an animal (preferably a mouse) with a huXAG-1, huXAG-2 or huXAG-3 protein antigen or, more preferably, with a huXAG-1, huXAG-2 or huXAG-3 protein-expressing cell. Suitable cells can be recognized by their capacity to bind anti-huXAG-1, anti-huXAG-2 or anti-huXAG-3 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (*Gastroenterology* 80:225-232 (1981)). The hybridoma cells obtained through such a selection are then assayed to identify clones which secrete antibodies capable of binding a huXAG-1, huXAG-2 or huXAG-3 protein antigen.

Alternatively, additional antibodies capable of binding to a huXAG-1, huXAG-2 or huXAG-3 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, huXAG-1-, huXAG-2- or huXAG-3-protein specific antibodies are used to immunize an animal, preferably a mouse. The splenocytes of such an animal are then used to produce hybridoma cells, and the hybridoma cells are screened to identify clones which produce an antibody whose ability to bind to a huXAG-1, huXAG-2 or huXAG-3 protein-specific antibody can be blocked by a huXAG-1, huXAG-2 or huXAG-3 protein antigen, respectively. Such antibodies comprise anti-idiotypic antibodies to a huXAG-1, huXAG-2 or huXAG-3 protein-specific antibody and can be used to immunize an animal to induce formation of further huXAG-1, huXAG-2 or huXAG-3 protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, huXAG-1, huXAG-2 or huXAG-3 protein-binding fragments can be produced through the application of recombinant DNA technology or through synthetic chemistry.

Where in vivo imaging is used to detect enhanced levels of huXAG-1, huXAG-2 or huXAG-3 protein for tumor diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the huXAG-1, huXAG-2 or huXAG-3 protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{99m}$Tc, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In and $^{99m}$Tc are preferred isotopes where in vivo imaging is used since it avoids the problem of dehalogenation of the $^{125}$I or 131I-labeled monoclonal antibody by the liver. In addition, theses radionucleotides have a more favorable gamma emission energy for imaging (Perkins et al., *Eur. J. Nucl. Med.* 10:296-301 (1985); Carasquillo et al., *J. Nucl. Med.* 28:281-287 (1987)). For example, $^{111}$In coupled to monoclonal antibodies with 1-(p-isothiocyanatobenzyl)-DPTA has shown little uptake in non-tumorous tissues, particularly the liver, and therefore enhances specificity of tumor localization (Esteban et al., *J. Nucl. Med.* 28:861-870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1-31 (1976), and Schurs et al., *Clin. Chim. Acta* 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

The polypeptides of the present invention are growth factors and, as such, can be used to stimulate proliferation of cells, for example, colon, breast, liver, and lung cells.

Due to the homology of huXAG-1, huXAG-2 and huXAG-3 with *Xenopus* XAG these genes are believed to be morphogens involved with growth and development of the human embryo and also in adult life. Further, these genes are highly expressed in many tumor types including osteoclastoma, breast cancer, colon cancer, and hepatocellular carcinoma. They are also expressed in the human lung.

The polypeptides of the present invention can be employed to stimulate proliferation and differentiation of hepatocytes, and thus, could be used to alleviate or treat liver diseases and pathologies such as fulminant liver failure caused by cirrhosis, liver damage caused by viral hepatitis and toxic substances (i.e., acetaminophen, carbon tetrachloride and other hepatotoxins known in the art). The polypeptides of the present invention can also be used to stimulate or promote liver regeneration, for example, after surgery.

The polypeptides of the present invention can be used to prevent and heal damage to the lungs caused by various pathological states. As growth factors, the polypeptides of the present invention could stimulate proliferation and differentiation and promote the repair of alveoli and bronchiolar epithelium to prevent, attenuate, or treat acute or chronic lung damage. For example, emphysema, which results in the progressive loss of alveoli, and inhalation injuries, i.e., resulting from smoke inhalation and burns, that cause necrosis of the bronchiolar epithelium and alveoli could be effectively treated using the polypeptides of the present invention. huXAG-3 is preferably employed to promote the growth of lung tissue.

The polypeptides of the present invention could also stimulate the proliferation and differentiation of breast tissue and could therefor be used to promote healing of breast tissue injury due to surgery, trauma, or cancer.

This invention also provides a method for identification of the receptors for a huXAG-1, huXAG-2 or huXAG-3 polypeptide. The gene encoding the receptor can be identified by numerous methods known to those of skill in the art, for example, ligand panning and FACS sorting (Coligan et al., *Current Protocols in Immun.*, 1(2), *Chapter* 5 (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an iterative sub-pooling and rescreening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to x-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

This invention provides a method of screening compounds to identify those which agonize the action of huXAG-1, huXAG-2 or huXAG-3 or block the function of huXAG-1, huXAG-2 or huXAG-3. An example of such an assay comprises combining a mammalian cell, for example, a colon cell, the compound to be screened and $^3$[H] thymidine under cell culture conditions where the cell would normally proliferate. A control assay may be performed in the absence of the compound to be screened and compared to the amount of cellular proliferation in the presence of the compound to determine if the compound stimulates cellular proliferation.

To screen for antagonists, the same assay may be prepared in the presence of huXAG-1, huXAG-2 or huXAG-3 and the ability of the compound to prevent cellular proliferation is measured and a determination of antagonist ability is made.

The amount of cellular proliferation is measured by liquid scintillation chromatography which measures the incorporation of $^3$[H] thymidine.

In another method, a mammalian cell or membrane preparation expressing a huXAG-1, huXAG-2 or huXAG-3 receptor would be incubated with labeled huXAG-1, huXAG-2 or huXAG-3 in the presence of the compound. The ability of the compound to enhance or block this interaction could then be measured. Alternatively, the response of a known second messenger system following interaction of huXAG-1, huXAG-2 or huXAG-3 and receptor would be measured and compared in the presence or absence of the compound. Such second messenger systems include but are not limited to, cAMP guanylate cyclase, ion channels or phosphoinositide hydrolysis.

Examples of potential huXAG-1, huXAG-2 or huXAG-3 antagonists include an antibody, or in some cases, an oligonucleotide, which binds to the polypeptide. Alternatively, a potential huXAG-1, huXAG-2 or huXAG-3 antagonist may be a mutant form of huXAG-1, huXAG-2 or huXAG-3 which binds to huXAG-1, huXAG-2 or huXAG-3 receptors, yet elicits no second messenger response. Therefore the action of huXAG-1, huXAG-2 or huXAG-3 is effectively blocked.

Antagonists of huXAG-1, huXAG-2 or huXAG-3 are contemplated to be useful for inhibiting tumor growth. Tumor growth that is related to the misexpression of a developmental morphogen, such as huXAG-1, huXAG-2 or huXAG-3 can be decreased or prevented by turning off the expression of these polypeptides in adult tissue.

Another potential huXAG-1, huXAG-2 or huXAG-3 antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)), thereby preventing transcription and the production of huXAG-1, huXAG-2 or huXAG-3. The antisense RNA oligonucleotide hybridizes to the cDNA in vivo and blocks translation of the cDNA molecule into huXAG-1, huXAG-2 or huXAG-3 polypeptide (Antisense—Okano, *J., Neurochem.* 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of huXAG-1, huXAG-2 or huXAG-3.

Potential huXAG-1, huXAG-2 or huXAG-3 antagonists include small molecules which bind to and occupy the binding site of a huXAG-1, huXAG-2 or huXAG-3 receptor thereby making the receptor inaccessible to huXAG-1, huXAG-2 or huXAG-3 such that normal biological activity is prevented. Examples of small molecules include but are not limited to small peptides or peptide-like molecules.

Antagonists of huXAG-1, huXAG-2 or huXAG-3 can be employed to treat hyperproliferative disorders, including cancer, in particular hepatocellular carcinoma, osteoclastoma, breast cancer, and colon cancer.

Modes of Administration

It will be appreciated that conditions caused by a decrease in the standard or normal level of huXAG-1, huXAG-2 or huXAG-3 activity in an individual, or conditions that can be ameliorated by enhanced levels of huXAG-1, huXAG-2 or huXAG-3 activity, can be treated by administration of huXAG-1, huXAG-2 or huXAG-3 protein, respectively. Thus, the invention further provides a method of treating an individual in need of an increased level of huXAG-1, huXAG-2 or huXAG-3 activity comprising administering to such an individual a pharmaceutical composition comprising an effective amount of an isolated huXAG-1, huXAG-2 or huXAG-3 polypeptide of the invention, respectively. Particularly preferred is a mature form of the huXAG-1, huXAG-2 or huXAG-3 protein, effective to increase the huXAG-1, huXAG-2 or huXAG-3 activity level in such an individual. Such treatments are contemplated to be particularly useful in the stimulation of tissue regrowth in the lungs, liver, colon and bones.

The huXAG-1, huXAG-2 or huXAG-3 polypeptide composition will be formulated and dosed in a fashion consistent with good medical practice, taking into account the clinical condition of the individual patient (especially the side effects of treatment with huXAG-1, huXAG-2 or huXAG-3 polypeptide alone), the site of delivery of the huXAG-1, huXAG-2 or huXAG-3 polypeptide composition, the method of administration, the scheduling of administration, and other factors known to practitioners. The "effective amount" of huXAG-1, huXAG-2 or huXAG-3 polypeptide for purposes herein is thus determined by such considerations.

As a general proposition, the total pharmaceutically effective amount of huXAG-1, huXAG-2 or huXAG-3 polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the huXAG-1, huXAG-2 or huXAG-3 polypeptide is typically administered at a dose rate of about 1 μg/kg/hour to about 50 μg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing a huXAG-1, huXAG-2 or huXAG-3 polypeptide of the invention may be administered orally, rectally, parenterally, intracisternally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

A huXAG-1, huXAG-2 or huXAG-3 polypeptide is also suitably administered by sustained-release systems. Suitable examples of sustained-release compositions include semipermeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained-release huXAG-1, huXAG-2 or huXAG-3 polypeptide compositions also include liposomally entrapped huXAG-1, huXAG-2 or huXAG-3 polypeptide. Liposomes containing huXAG-1, huXAG-2 or huXAG-3 polypeptide are prepared by methods known per se: DE 3,218,121; Epstein et al., *Proc. Natl. Acad. Sci.* (*USA*) 82:3688-3692 (1985); Hwang et al., *Proc. Natl. Acad. Sci.* (*USA*) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal huXAG-1, huXAG-2 or huXAG-3 polypeptide therapy.

For parenteral administration, in one embodiment, a huXAG-1, huXAG-2 or huXAG-3 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting a huXAG-1, huXAG-2 or huXAG-3 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

A huXAG-1, huXAG-2 or huXAG-3 polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of huXAG-1, huXAG-2 or huXAG-3 polypeptide salts.

A huXAG-1, huXAG-2 or huXAG-3 polypeptide to be used for therapeutic administration must be sterile. Sterility is readily accomplished by filtration through sterile filtration membranes (e.g., 0.2 micron membranes). Therapeutic huXAG-1, huXAG-2 or huXAG-3 polypeptide compositions generally are placed into a container having a sterile access port, for example, an intravenous solution bag or vial having a stopper pierceable by a hypodermic injection needle.

A huXAG-1, huXAG-2 or huXAG-3 polypeptide ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous huXAG-1, huXAG-2 or huXAG-3 polypeptide solution, and the resulting mixture is lyophilized. The infusion solution is prepared by reconstituting the lyophilized huXAG-1, huXAG-2 or huXAG-3 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Chromosome Assays

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a huXAG-1, huXAG-2 or huXAG-3 protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In addition, in some cases, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb.

Having generally described the invention, the same will be more readily understood by reference to the following examples, which are provided by way of illustration and are not intended as limiting.

EXAMPLE 1

Expression and Purification of huXAG-1 Polypeptide in *E. coli*

The DNA sequence encoding the mature huXAG-1 in the deposited cDNA clone was amplified using PCR oligonucleotide primers specific to the amino terminal sequences of the huXAG-1 and to vector sequences 3' to the gene. Additional nucleotides containing restriction sites to facilitate cloning were added to the 5' and 3' sequences respectively.

The 5' oligonucleotide primer had the sequence 5'CGC CCATGG GCC AGA GAT ACC ACA G 3' (SEQ ID NO:23) containing the underlined NcoI restriction site.

The 3' primer had the sequence 5'CGC AAGCTT TTA CAA TTC AGT CTT CAG C 3' (SEQ ID NO:24) containing the underlined HindIII restriction site.

Alternatively, the following primers can be used:

```
5' primer:
                                      (SEQ ID NO:42)
5' GACCGC TCATGA GAG ATA CCA CAG TCA AAC CTG GAG
CCA AAA AG 3'

3' primer:
                                      (SEQ ID NO:43)
5' GACCGC AAGCTT GAA GGG CTT GGA GAT TTT TTT TTA
TTA CAA TTC 3'
```

The restriction sites are convenient to restriction enzyme sites in the bacterial expression vector pQE60, which was used for bacterial expression in M15/rep4 host cells in these examples. (Qiagen, Inc., Chatsworth, Calif., 91311). pQE60 encodes ampicillin antibiotic resistance ("Amp<sup>r</sup>") and contains a bacterial origin of replication ("ori"), an IPTG inducible promoter, a ribosome binding site ("RBS"), a 6-His tag and restriction enzyme sites.

The amplified huXAG-1 DNA and the vector pQE60 both were digested with NcoI and HindIII and the digested DNAs were then ligated together. Insertion of the huXAG-1 DNA into the restricted pQE60 vector placed the huXAG-1 coding region downstream of and operably linked to the vector's IPTG-inducible promoter and in-frame with an initiating ATG appropriately positioned for translation of huXAG-1.

The ligation mixture was transformed into competent *E. coli* cells using standard procedures. Such procedures are described in Sambrook et al., *Molecular Cloning: A Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses lac repressor and confers kanamycin resistance ("Kan<sup>r</sup>"), was used in carrying out the illustrative example described here. This strain, which is only one of many that are suitable for expressing huXAG-1, is available commercially from Qiagen.

Transformants were identified by their ability to grow on LB plates in the presence of ampicillin and kanamycin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 μg/ml) and kanamycin (25 μg/ml).

The O/N culture was used to inoculate a large culture, at a dilution of approximately 1:100 to 1:250. The cells were grown to an optical density at 600 nm ("OD600") of between 0.4 and 0.6. Isopropyl-B-D-thiogalactopyranoside ("IPTG") was then added to a final concentration of 1 mM to induce transcription from lac repressor sensitive promoters, by inactivating the lacI repressor. Cells subsequently were incubated further for 3 to 4 hours. Cells were then harvested by centrifugation and disrupted, by standard methods. Inclusion bodies were purified from the disrupted cells using routine collection techniques, and protein was solubilized from the inclusion bodies into 8M urea. The 8M urea solution containing the solubilized protein was passed over a PD-10 column in 50 mM Tris (pH 7.0)+400 or 200 mM NaCl, thereby removing the urea, exchanging the buffer and refolding the protein. The protein was purified by a further step of chromatography to remove endotoxin. Then, it was sterile filtered. The sterile filtered protein preparation was stored in the above Tris buffer.

Analysis of the preparation by standard methods of polyacrylamide gel electrophoresis revealed that the preparation contains about 90% monomer huXAG-1 having the expected molecular weight of approximately 16 kDa.

EXAMPLE 2

Expression and Purification of huXAG-2 Polypeptide in *E. coli*

The DNA sequence encoding the mature huXAG-2 in the deposited cDNA clone was amplified using PCR oligonucleotide primers specific to the amino terminal sequences of the huXAG-2 and to vector sequences 3' to the gene. Additional nucleotides containing restriction sites to facilitate cloning were added to the 5' and 3' sequences respectively.

The 5' oligonucleotide primer had the sequence 5' GAC CGC ACATGT TCT GAT GGA CAT AAT GGG CTT GGA AAG GGT TTT G 3' (SEQ ID NO:25) containing the underlined AflII restriction site.

The 3' primer had the sequence 5' GAC CGC AAGCTT CTC TGA TGA AAG AAG GGG CAC ATT CTT ATT ACA ATT C3' (SEQ ID NO:26) containing the underlined HindIII restriction site.

The restriction sites are convenient to restriction enzyme sites in the bacterial expression vector pQE60, which was used for bacterial expression in M15/rep4 host cells in these examples. (Qiagen, Inc., Chatsworth, Calif., 91311). pQE60 encodes ampicillin antibiotic resistance ("Ampr") and contains a bacterial origin of replication ("ori"), an IPTG inducible promoter, a ribosome binding site ("RBS"), a 6-His tag and restriction enzyme sites.

The amplified huXAG-2 DNA and the vector pQE60 both were digested with AflIII and HindIII and the digested DNAs were then ligated together. Insertion of the huXAG-2 DNA into the restricted pQE60 vector placed the huXAG-2 coding region downstream of and operably linked to the vector's IPTG-inducible promoter and in-frame with an initiating ATG appropriately positioned for translation of huXAG-2.

Transformation of *E. coli*, expression and purification of huXAG-2 were carried out according to the procedures set forth in Example 1.

EXAMPLE 3

Expression and Purification of huXAG-3 Polypeptide in *E. coli*

The DNA sequence encoding the mature huXAG-3 in the deposited cDNA clone was amplified using PCR oligonucleotide primers specific to the amino terminal sequences of the huXAG-3 and to vector sequences 3' to the gene. Additional nucleotides containing restriction sites to facilitate cloning were added to the 5' and 3' sequences respectively.

The 5' oligonucleotide primer had the sequence 5' GAC CGC TCATGA ATA AAA AAG GAA AAG AGG CCT CCT CAG ACA CTC 3' (SEQ ID NO:27) containing the underlined BspHI restriction site.

The 3' primer had the sequence 5' GAC CGC AAGCTT CTT TGA AGT GAA GGC TTT TTT CTA TCA TTT ATT ATA G 3' (SEQ ID NO:28) containing the underlined HindIII restriction site.

The restriction sites are convenient to restriction enzyme sites in the bacterial expression vector pQE60, which was used for bacterial expression in M15/rep4 host cells in these examples. (Qiagen, Inc., Chatsworth, Calif., 91311). pQE60 encodes ampicillin antibiotic resistance ("Amp'") and contains a bacterial origin of replication ("ori"), an IPTG inducible promoter, a ribosome binding site ("RBS"), a 6-His tag and restriction enzyme sites.

The amplified huXAG-3 DNA and the vector pQE60 both were digested with BspHI and HindIII and the digested DNAs were then ligated together. Insertion of the huXAG-3 DNA into the restricted pQE60 vector placed the huXAG-3 coding region downstream of and operably linked to the vector's IPTG-inducible promoter and in-frame with an initiating ATG appropriately positioned for translation of huXAG-3.

Transformation of *E. coli*, expression and purification of huXAG-3 were carried out according to the procedures set forth in Example 1.

EXAMPLE 4

Cloning and Expression of huXAG-1 in a Baculovirus Expression System

The cDNA sequence encoding the full length huXAG-1 in the deposited clone is amplified using PCR oligonucleotide primers corresponding to the 5' and 3' sequences of the gene:

The 5' primer has the sequence 5'CGC GGATCC GCC ATC ATG GAG AAA ATT CCA GTG 3' (SEQ ID NO:29) containing the underlined BamHI restriction enzyme site followed by eighteen bases of the sequence of huXAG-1 in FIG. 1. Inserted into an expression vector, as described below, the 5' end of the amplified fragment encoding huXAG-1 provides an efficient signal peptide. An efficient signal for initiation of translation in eukaryotic cells, as described by Kozak, M., *J. Mol. Biol.* 196:947-950 (1987) is appropriately located in the vector portion of the construct.

The 3' primer has the sequence 5'CGC GGATCC TTA CAA TTC AGT CTT CAG C3' (SEQ ID NO:30) containing the underlined BamHI restriction site followed by nucleotides complementary to the last nineteen nucleotides of the huXAG-1 coding sequence set out in FIG. 1.

Alternatively, the following primers may be used:

```
5' primer:
                                         (SEQ ID NO:44)
5' GACT GGATCC GCCATC ATG GAG AAA ATT CCA GTG TCA
GCA TTC TTG CTC 3'

3' primer:
                                         (SEQ ID NO:45)
5' GACT GGTACC GGA GAT TTT TTT TCT TTA CAA TTC AGT
CTT CAG 3'
```

The amplified fragment is isolated from a 1% agarose gel using a commercially available kit ("Geneclean," BIO 101 Inc., La Jolla, Calif.). The fragment then is digested with BamHI and again is purified on a 1% agarose gel. This fragment is designated herein F2.

The vector pA2-GP is used to express huXAG-1 in the baculovirus expression system, using standard methods, as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170: 31-39, among others.

The plasmid is digested with the restriction enzyme BamHI and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the huXAG-1 gene by digesting DNA from individual colonies using XbaI and then analyzing the digestion product by gel electrophoresis. The sequence of the cloned fragment is confirmed by DNA sequencing. This plasmid is designated herein pBac huXAG-1.

5 μg of the plasmid pBac huXAG-1 is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413-7417 (1987). 1 μg of BaculoGold™ virus DNA and 5 μg of the plasmid pBac huXAG-1 are mixed in a sterile well of a microtiter plate containing 50 μl of serum-free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted hESSB I, II and III is identified by DNA analysis including restriction mapping and sequencing. This is designated herein as V-huXAG-1.

Sf9 cells are grown in Grace's medium supplemented with 10% heat-inactivated FBS. The cells are infected with the recombinant baculovirus V-huXAG-1 at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 μCi of $^{35}$S-methionine and 5 μCi $^{35}$S-cysteine (available from Amersham) are added. The cells are further incubated for 16 hours and then they are harvested by centrifugation, lysed and the labeled proteins are visualized by SDS-PAGE and autoradiography.

EXAMPLE 5

Cloning and Expression of huXAG-2 Protein in a Baculovirus Expression System

In this illustrative example, the plasmid shuttle vector pA2 is used to insert the cloned DNA encoding the complete protein, including its naturally associated secretary signal (leader) sequence, into a baculovirus to express the mature huXAG-2 protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39.

The cDNA sequence encoding the full length huXAG-2 protein in the deposited clone, including the AUG initiation codon and the naturally associated leader sequence shown in FIG. 2 (SEQ ID NO:4), is amplified using PCR oligonucleotide primers corresponding to the 5' and 3' sequences of the gene. The 5' primer has the sequence 5' GACT TGATCA GCC ATC ATG GAG ACG CGG CCT CGT CTC GGG GCC ACC TG 3' (SEQ ID NO:31) containing the underlined BclI restriction enzyme site, an efficient signal for initiation of translation in eukaryotic cells, as described by Kozak, M., *J. Mol. Biol.* 196:947-950 (1987), followed by 32 bases of the sequence of the complete huXAG-2 protein shown in FIG. 2, beginning with the AUG initiation codon. The 3' primer has the sequence 5' GACT GGTACC GAA GGG GCA CAT TCA TGT TAC AAT TCA TCT TCA AG 3' (SEQ ID NO:32) containing the underlined, Asp718I restriction site followed by 35 nucleotides complementary to the 3' sequence in FIG. 2.

The amplified fragment is isolated from a 1% agarose gel using a commercially available kit ("Geneclean," BIO 101 Inc., La Jolla, Calif.). The fragment then is digested with BclI and Asp718I and again is purified on a 1% agarose gel. This fragment is designated herein "F1".

The plasmid is digested with the restriction enzymes BclI and Asp718I and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the huXAG-2 gene using the PCR method, in which one of the primers that is used to amplify the gene and the second primer is from well within the vector so that only those bacterial colonies containing the huXAG-2 gene fragment will show amplification of the DNA. The sequence of the cloned fragment is confirmed by DNA sequencing. This plasmid is designated herein pBachuXAG-2.

Five μg of the plasmid pBachuXAG-2 is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413-7417 (1987). 1 μg of BaculoGold™ virus DNA and 5 μg of the plasmid pBachuXAG-2 are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9-10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-huXAG-2.

To verify the expression of the huXAG-2 gene, Sf9 cells are grown in Grace's medium supplemented with 10% heat inactivated FBS. The cells are infected with the recombinant baculovirus V-huXAG-2 at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

EXAMPLE 6

Cloning and Expression of huXAG-3 Protein in a Baculovirus Expression System

In this illustrative example, the plasmid shuttle vector pA2 is used to insert the cloned DNA encoding the complete protein, including its naturally associated secretory signal (leader) sequence, into a baculovirus to express the mature huXAG-3 protein, using standard methods as described in Summers et al., *A Manual of Methods for Baculovirus Vectors and Insect Cell Culture Procedures*, Texas Agricultural Experimental Station Bulletin No. 1555 (1987).

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39.

The cDNA sequence encoding the full length huXAG-3 protein in the deposited clone, including the AUG initiation codon and the naturally associated leader sequence shown in FIG. 3 (SEQ ID NO:6), is amplified using PCR oligonucleotide primers corresponding to the 5' and 3' sequences of the gene. The 5' primer has the sequence 5' GACT <u>GGATCC</u> GCC ATC ATG ATG CTA CAC TCA GCT TTG GGT CTC TGC CTC 3' (SEQ ID NO:33) containing the underlined BamHI restriction enzyme site, an efficient signal for initiation of translation in eukaryotic cells, as described by Kozak, M., *J. Mol. Biol.* 196:947-950 (1987), followed by 33 bases of the sequence of the complete huXAG-3 protein shown in FIG. 3, beginning with the AUG initiation codon. The 3' primer has the sequence 5' GACT <u>GGTACC</u> GAA GGC TTT TTT CTA TCA TCT CTT ATA GCT CCT CAT ATG 3' (SEQ ID NO:34) containing the underlined, Asp718I restriction site followed by 31 nucleotides complementary to the 3' sequence in FIG. 3.

The amplified fragment is isolated from a 1% agarose gel using a commercially available kit ("Geneclean," BIO 101 Inc., La Jolla, Calif.). The fragment then is digested with BamHI and Asp718I and again is purified on a 1% agarose gel. This fragment is designated herein "F1".

The plasmid is digested with the restriction enzymes BamHI and Asp718I and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Formation of recombinant virus and expression and purification of huXAG-3 is carried out according to the procedures described in Example 5.

EXAMPLE 7

Cloning and Expression of huXAG-1, huXAG-2 and huXAG-3 in Mammalian Cells

Most of the vectors used for the transient expression of the huXAG-1, huXAG-2 or huXAG-3 gene sequences in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of trancription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 283, H9 and Jurkat cells, mouse NIH3T3 and C127 cells, Cos 1, Cos 7 and CV1, African green monkey cells, quail QC1-3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., Biochem J. 227:277-279 (1991); Bebbington et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., Molecular and Cellular Biology, 438-447 (March, 1985)) plus a fragment of the CMV-enhancer (Boshart et al., Cell 41:521-530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

EXAMPLE 7(A)

Cloning and Expression of huXAG-1 in COS Cells

The expression plasmid, phuXAG-1 HA, is made by cloning a cDNA encoding huXAG-1 into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767-778 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding huXAG-1 is cloned into the polylinker region of the vector so that recombinant protein expression is directed by the CMV promoter. The plasmid construction strategy is as follows. The huXAG-1 cDNA of the deposited clone is amplified using primers that contain convenient restriction sites, much as described above for construction of vectors for expression of huXAG-1 in *E. coli*. Suitable primers include the following, which are used in this example. The 5' primer, containing the underlined BamHI site, a Kozak sequence, an AUG start codon and 18 bp of the 5' coding region of the complete huXAG-1 has the following sequence: 5' CGC GGATCC GCC ATC ATG GAG AAA ATT CCA GTG 3' (SEQ ID NO:29). The 3' primer, containing the underlined BamHI site, a stop codon, and 19 bp of 3' coding sequence has the following sequence (at the 3' end): 5' CGC GGATCC TTA CAA TTC AGT CTT CAG C3' (SEQ ID NO:30).

Alternatively, the following primers may be used:

```
5' primer:
                                           (SEQ ID NO:44)
5' GACT GGATCC GCCATC ATG GAG AAA ATT CCA GTG TCA
GCA TTC TTG CTC 3'

3' primer:
                                           (SEQ ID NO:45)
5' GACT GGTACC GGA GAT TTT TTT TCT TTA CAA TTC AGT
CTT CAG 3'
```

The PCR amplified DNA fragment and the vector, pcDNAI/Amp, are digested with BamHI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the huXAG-1-encoding fragment.

For expression of recombinant huXAG-1, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of huXAG-1 by the vector.

Expression of the huXAG-1-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

EXAMPLE 7(B)

Cloning and Expression of huXAG-2 in COS Cells

The expression plasmid, phuXAG-2 HA, is made by cloning a cDNA encoding huXAG-2 into the expression vector pcDNAI/Amp or pcDNAIII (which can be obtained from Invitrogen, Inc.).

A DNA fragment encoding huXAG-2 is cloned into the polylinker region of the vector so that recombinant protein expression is directed by the CMV promoter. The plasmid construction strategy is as follows. The 5' primer, containing the underlined site, a Kozak sequence, an AUG start codon and 32 bp of the 5' coding region of the complete huXAG-2 has the following sequence: 5' GACT <u>TGATCA</u> GCC ATC ATG GAG ACG CGG CCT CGT CTC GGG GCC ACC TG 3' (SEQ ID NO:31). The 3' primer, containing the underlined Asp718I site, a stop codon, and 35 bp of 3' coding sequence has the following sequence (at the 3' end): 5' GACT <u>GGTACC</u> GAA GGG GCA CAT TCA TGT TAC AAT TCA TCT TCA AG 3' (SEQ ID NO:32).

The PCR amplified DNA fragment and the vector, pcD-NAI/Amp, are digested with BamHI and Asp718I and then ligated. The ligation mixture is transformed into *E. coli* strain SURE (Stratagene Cloning Systems), and the—transformed culture is plated on ampicillin media plates which then are incubated to allow growth of ampicillin resistant colonies. Plasmid DNA is isolated from resistant colonies and examined by restriction analysis or other means for the presence of the huXAG-2-encoding fragment.

For expression of recombinant huXAG-2, COS cells are transfected with an expression vector, as described above. Cells are incubated under conditions for expression of huXAG-2 by the vector.

Expression of the huXAG-2-HA fusion protein is detected by radiolabeling and immunoprecipitation, using methods described above. To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

EXAMPLE 7(C)

Cloning and Expression of huXAG-3 in COS Cells

The expression plasmid, phuXAG-3 HA, is made by cloning a cDNA encoding huXAG-3 into the expression vector pcDNAI/Amp or pcDNAIII (which can be obtained from Invitrogen, Inc.).

A DNA fragment encoding huXAG-3 is cloned into the polylinker region of the vector so that recombinant protein expression is directed by the CMV promoter. The plasmid construction strategy is as follows. The 5' primer, containing the underlined BamHI site, a Kozak sequence, an AUG start codon and 33 bp of the 5' coding region of the complete huXAG-3 has the following sequence: 5' GACT <u>GGATCC</u> GCCATC ATG ATG CTA CAC TCA GCT TTG GGT CTC TGC CTC 3' (SEQ ID NO:33). The 3' primer, containing the underlined Asp718I site, a stop codon, and 31 bp of 3' coding sequence has the following sequence (at the 3' end): 5' GACT <u>GGTACC</u> GAA GGC TTT TTT CTA TCA TCT CTT ATA GCT CCT CAT ATG 3' (SEQ ID NO:34).

The PCR amplified DNA fragment and the vector, pcD-NAI/Amp, are digested with BamHI and Asp718I and then ligated. The ligation mixture is transformed into *E. coli* strain SURE (Stratagene Cloning Systems), and the transformed culture is plated on ampicillin media plates which then are incubated to allow growth of ampicillin resistant colonies. Plasmid DNA is isolated from resistant colonies and examined by restriction analysis or other means for the presence of the huXAG-3-encoding fragment.

For expression of recombinant huXAG-3, COS cells are transfected with an expression vector, using DEAE-DEXTRAN. Cells are incubated under conditions for expression of huXAG-3 by the vector.

Expression of the huXAG-3-HA fusion protein is detected by radiolabeling and immunoprecipitation, using methods described above. To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

EXAMPLE 7(D)

Cloning and Expression of huXAG-1 in CHO Cells

The vector pC4 is used for the expression of huXAG-1 protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357-1370, Hamlin, J. L. and Ma, C. 1990, *Biochem. et Biophys. Acta,* 1097:107-143, Page, M. J. and Sydenham, M. A. 1991, *Biotechnology* 9:64-68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molec. Cell. Biol.* 5:438-447 (1985)) plus a fragment isolated from the enhancer of the immediate early gene of human cytomegalovirus (CMV) (Boshart et al., *Cell* 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the huXAG-1 in a regulated way in mammalian cells (Gossen, M., & Bujard, H. 1992, *Proc. Natl. Acad. Sci. USA* 89: 5547-5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzyme BamHI and then dephosphorylated using calf intestinal phosphatase by procedures known in the art. The vector is then isolated from a 1% agarose gel.

The DNA sequence encoding the complete huXAG-1 protein including its leader sequence is amplified using PCR oligonucleotide primers corresponding to the 5' and 3' sequences of the gene. The 5' primer has the sequence 5'CGC GGATCC GCC ATC ATG GAG AAA ATT CCA GTG 3' (SEQ ID NO:29) containing the underlined BamHI restriction enzyme site followed by an efficient signal for initiation of translation in eukaryotes, as described by Kozak, M., *J. Mol. Biol.* 196:947-950 (1987), and 18 bases of the coding sequence of huXAG-1 shown in FIG. 1 (SEQ ID NO:1). The 3' primer has the sequence 5'CGC GGATCC TTA CAA TTC AGT CTT CAG C 3' (SEQ ID NO:30) containing the underlined BamHI restriction site followed by 19 nucleotides complementary to the non-translated region of the huXAG-1 gene shown in FIG. 1 (SEQ ID NO:1).

Alternatively, the following primers may be used:

```
5' primer:
                                              (SEQ ID NO:44)
5' GACT GGATCC GCCATC ATG GAG AAA ATT CCA GTG TCA
GCA TTC TTG CTC 3'

3' primer:
                                              (SEQ ID NO:45)
5' GACT GGTACC GGA GAT TTT TTT TCT TTA CAA TTC AGT
CTT CAG 3'
```

The amplified fragment is digested with the endonuclease BamHI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100-200 μM. Expression of the desired gene product is analyzed, for instance, by SDS-PAGE and Western blot or by reverse phase HPLC analysis.

EXAMPLE 7(E)

Cloning and Expression of huXAG-2 in CHO Cells

The vector pC4 is used for the expression of huXAG-2 protein. The plasmid pC4 is digested with the restriction enzymes BclI and Asp718I and then dephosphorylated using calf intestinal phosphatase by procedures known in the art. The vector is then isolated from a 1% agarose gel.

The DNA sequence encoding the complete huXAG-2 protein including its leader sequence is amplified using PCR oligonucleotide primers corresponding to the 5' and 3' sequences of the gene. The 5' primer has the sequence 5' GACT TGATCA GCCATC ATG GAG ACG CGG CCT CGT CTC GGG GCC ACC TG 3' (SEQ ID NO:31) containing the underlined BclI restriction enzyme site followed by an efficient signal for initiation of translation in eukaryotes, as described by Kozak, M., *J. Mol. Biol.* 196:947-950 (1987), and 32 bases of the coding sequence of huXAG-2 shown in FIG. 2 (SEQ ID NO:3). The 3' primer has the sequence 5' GACT GGTACC GAA GGG GCA CAT TCA TGT TAC AAT TCA TCT TCA AG 3' (SEQ ID NO: 32) containing the underlined Asp718I restriction site followed by 35 nucleotides complementary to the non-translated region of the huXAG-2 gene shown in FIG. 2 (SEQ ID NO:3).

The amplified fragment is digested with the endonucleases BclI and Asp718I and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100-200 μM. Expression of the desired gene product is analyzed, for instance, by SDS-PAGE and Western blot or by reverse phase HPLC analysis.

EXAMPLE 7(F)

Cloning and Expression of huXAG-3 in CHO Cells

The vector pC4 is also used for the expression of huXAG-3 protein. The plasmid pC4 is digested with the restriction enzymes BamHI and Asp718I and then dephosphorylated using calf intestinal phosphatase by procedures known in the art. The vector is then isolated from a 1% agarose gel.

The DNA sequence encoding the complete huXAG-3 protein including its leader sequence is amplified using PCR oligonucleotide primers corresponding to the 5' and 3' sequences of the gene. The 5' primer has the sequence 5' GACT GGATCC GCC ATC ATG ATG CTA CAC TCA GCT TTG GGT CTC TGC CTC 3' (SEQ ID NO:33) containing the underlined BamHI restriction enzyme site followed by an efficient signal for initiation of translation in eukaryotes, as described by Kozak, M., *J. Mol. Biol.* 196:947-950 (1987), and 33 bases of the coding sequence of huXAG-3 shown in FIG. 3 (SEQ ID NO:5). The 3' primer has the sequence 5'GACT GGTACC GAA GGC TTT TTT CTA TCA TCT CTT ATA GCT CCT CAT ATG 3' (SEQ ID NO:34) containing the underlined Asp718I restriction site followed by 31 nucleotides complementary to the non-translated region of the huXAG-3 gene shown in FIG. 3 (SEQ ID NO:5).

The amplified fragment is digested with the endonucleases BamHI and Asp718I and then purified again on a 1% agarose gel. The isolated fragment and the dephosphorylated vector are then ligated with T4 DNA ligase. *E. Coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100-200 μM. Expression of the desired gene product is analyzed, for instance, by SDS-PAGE and Western blot or by reverse phase HPLC analysis.

EXAMPLE 8

Tissue Distribution of huXAG-1 mRNA Expression

Northern blot analysis was carried out to examine the levels of expression of the gene encoding huXAG-1 in human tissues, using methods described by, among others, Sambrook et al., cited above. A cDNA probe containing the entire nucleotide sequence of the huXAG-1 protein of the present invention (SEQ ID NO:1) was labeled with $^{32}P$ using the rediprime™ DNA labeling system (Amersham Life Science), according to manufacturer's instructions. After labelling, the probe was purified using a CHROMA SPIN-100™ column (Clontech Laboratories, Inc.), according to manufacturer's protocol number PT1200-1. The purified labelled probe was then used to examine various human tissues for the expression of the gene encoding the huXAG-1.

Multiple Tissue Northern (MTN) blots containing various human tissues (H) or human immune system tissues (IM) are obtained from Clontech and were examined with labelled probe using ExpressHyb™ Hybridization Solution (Clontech) according to manufacturer's protocol number PT1190-1. Following hybridization and washing, the blots were mounted and exposed to film at −70° C. overnight, and films developed according to standard procedures. A signal was detected in cells derived from a human colon carcinoma. No signal was detected in any other tissue further confirming the gene is colon cancer specific.

EXAMPLE 9

Tissue Distribution of huXAG-2 mRNA Expression

Northern blot analysis was carried out to examine huXAG-2 gene expression in human tissues, using methods described in Example 8. The expression of huXAG-2 was found to be ubiquitous.

EXAMPLE 10

Tissue Distribution of huXAG-3 mRNA Expression

Northern blot analysis was carried out to examine huXAG-3 gene expression in human tissues, using methods described in Example 8. Expression was detected in colon, intestine, and lung tissue.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A diagnostic method comprising:
   (a) measuring the protein level of a polypeptide in a sample from an individual, wherein said sample is colon tissue, and wherein said polypeptide has an amino acid sequence at least 95% identical to a sequence selected from the group consisting of:
      (i) amino acids from about −20 to about 155 in SEQ ID NO:2;
      (ii) amino acids from about −19 to about 155 in SEQ ID NO:2;
      (iii) amino acids from about 1 to about 155 in SEQ ID NO:2;
      (iv) the amino acid sequence of a full-length polypeptide having the amino acid sequence encoded by the cDNA clone contained in ATCC Deposit No. 97641;
      (v) the amino acid sequence of a mature polypeptide having the amino acid sequence encoded by the cDNA clone contained in ATCC Deposit No. 97641; and
   (b) comparing said protein level of said individual with a standard huXAG-1 (SEQ ID NO: 2) protein level, whereby an increase or decrease in the protein level over said standard is indicative of the presence or absence of a huXAG-1-related disorder, wherein said protein level of said individual is detected with an antibody.

2. The diagnostic method of claim 1, wherein said sample is selected from the group consisting of cells, body fluid, and tissue.

3. The diagnostic method of claim 1, wherein detection with said antibody is an in vitro assay selected from the group consisting of immunohistochemical assay, enzyme linked immunoassay (ELISA), and radioimmunoassay (RIA).

4. The diagnostic method of claim 1, wherein detection with said antibody is an in vivo imaging assay selected from the group consisting of X-radiography, nuclear magnetic resonance (NMR), and electron spin resonance (ESR).

5. The diagnostic method of claim 1, wherein the antibody is a polyclonal antibody.

6. The diagnostic method of claim 1, wherein the antibody is a monoclonal antibody.

7. The diagnostic method of claim 3, comprising contacting huXAG-1 protein in said sample with an immobilized antibody to form a conjugate, and without washing, contacting said conjugate with a labeled antibody specific for huXAG-1.

8. The diagnostic method of claim 3, comprising contacting huXAG-1 protein in said sample with an immobilized antibody to form a conjugate, washing said immobilized antibody conjugate, and contacting the washed sample with a labeled antibody specific for huXAG-1.

9. The method of claim 1, wherein the huXAG-1-related disorder is colon cancer.

10. The method of claim 9, wherein the increase in the protein level over standard is indicative of colon cancer.

11. The method of claim 2, wherein the body fluid is from an individual suspected of having colon cancer.

12. The method of claim 9, wherein an equal level or decrease in the protein level over standard is indicative of a lack of colon cancer.

13. A method of diagnosing colon cancer in a subject comprising:
   a) collecting a biological sample from said subject;
   b) measuring huXAG-1 protein level in said biological sample, whereby said protein level is detected with an anti-huXAG-1 antibody, or portion thereof, which binds huXAG-1; and
   c) comparing said protein level with a standard from subjects that do not have colon cancer, wherein an enhanced protein level compared to said standard is indicative of the presence of colon cancer in said subject.

14. The method of claim 13, wherein said biological sample is colon tissue.

15. The diagnostic method of claim 13, wherein detection with said antibody is an in vitro assay selected from the group consisting of immunohistochemical assay, enzyme linked immunoassay (ELISA), and radioimmunoassay (RIA).

16. The diagnostic method of claim 13, comprising contacting huXAG-1 protein in said sample with an immobilized antibody to form a conjugate, washing said immobilized antibody conjugate, and contacting the washed sample with a labeled antibody specific for huXAG-1.

17. A method of diagnosing the clinical outcome in a colon cancer patient comprising:
   a) collecting a biological sample from said colon cancer patient;
   b) measuring huXAG-1 protein level in said biological sample, whereby said protein level is detected with an anti-huXAG-1 antibody, or portion thereof, which binds huXAG-1; and
   c) comparing said protein level with a standard from subjects that do not have colon cancer, wherein enhanced protein level compared to said standard is indicative of a worse clinical outcome relative to patients expressing the protein at lower levels.

18. The method of claim 17, wherein said biological sample is colon tissue.

19. The diagnostic method of claim 17, wherein detection with said antibody is an in vitro assay selected from the group consisting of immunohistochemical assay, enzyme linked immunoassay (ELISA), and radioimmunoassay (RIA).

20. The diagnostic method of claim 17, comprising contacting huXAG-1 protein in said sample with an immobilized antibody to form a conjugate, washing said immobilized antibody conjugate, and contacting the washed sample with a labeled antibody specific for huXAG-1.

\* \* \* \* \*

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
      (A) LENGTH: 875 base pairs
      (B) TYPE: nucleic acid
      (C) STRANDEDNESS: double
      (D) TOPOLOGY: linear (ii) MOLECULE TYPE: cDNA

```
    (ix) FEATURE:
          (A) NAME/KEY: CDS
          (B) LOCATION: 71..595

(ix) FEATURE:
          (A) NAME/KEY: mat_peptide
          (B) LOCATION: 131..595

(ix) FEATURE:
          (A) NAME/KEY: sig_peptide
          (B) LOCATION: 71..130

(xi) SEQUENCE DESCRIPTION: SEQ ID NO:1:

CGAGCGGCAC GAGCCGATTC CTAGCCGCCG ACTCACACAA GGCAGGTGGG TGAGGAAATC        60

CAGAGTTGCC ATG GAG AAA ATT CCA GTG TCA GCA TTC TTG CTC CTT GTG         109
           Met Glu Lys Ile Pro Val Ser Ala Phe Leu Leu Leu Val
               -20             -15                 -10

GCC CTC TCC TAC ACT CTG GCC AGA GAT ACC ACA GTC AAA CCT GGA GCC        157
Ala Leu Ser Tyr Thr Leu Ala Arg Asp Thr Thr Val Lys Pro Gly Ala
            -5                   1               5

AAA AAG GAC ACA AAG GAC TCT CGA CCC AAA CTG CCC CAG ACC CTC TCC        205
Lys Lys Asp Thr Lys Asp Ser Arg Pro Lys Leu Pro Gln Thr Leu Ser
 10                  15                  20                  25

AGA GGT TGG GGT GAC CAA CTC ATC TGG ACT CAG ACA TAT GAA GAA GCT        253
Arg Gly Trp Gly Asp Gln Leu Ile Trp Thr Gln Thr Tyr Glu Glu Ala
                 30                  35                  40

CTA TAT AAA TCC AAG ACA AGC AAC AAA CCC TTG ATG ATT ATT CAT CAC        301
Leu Tyr Lys Ser Lys Thr Ser Asn Lys Pro Leu Met Ile Ile His His
             45                  50                  55

TTG GAT GAG TGC CCA CAC AGT CAA GCT TTA AAG AAA GTG TTT GCT GAA        349
Leu Asp Glu Cys Pro His Ser Gln Ala Leu Lys Lys Val Phe Ala Glu
         60                  65                  70

AAT AAA GAA ATC CAG AAA TTG GCA GAG CAG TTT GTC CTC CTC AAT CTG        397
Asn Lys Glu Ile Gln Lys Leu Ala Glu Gln Phe Val Leu Leu Asn Leu
     75                  80                  85

GTT TAT GAA ACA ACT GAC AAA CAC CTT TCT CCT GAT GGC CAG TAT GTC        445
Val Tyr Glu Thr Thr Asp Lys His Leu Ser Pro Asp Gly Gln Tyr Val
 90                  95                 100                 105

CCC AGG ATT ATG TTT GTT GAC CCA TCT CTG ACA GTT AGA GCC GAT ATC        493
Pro Arg Ile Met Phe Val Asp Pro Ser Leu Thr Val Arg Ala Asp Ile
                110                 115                 120

ACT GGA AGA TAT TCA AAT CGT CTC TAT GCT TAC GAA CCT GCA GAT ACA        541
Thr Gly Arg Tyr Ser Asn Arg Leu Tyr Ala Tyr Glu Pro Ala Asp Thr
            125                 130                 135

GCT CTG TTG CTT GAC AAC ATG AAG AAA GCT CTC AAG TTG CTG AAG ACT        589
Ala Leu Leu Leu Asp Asn Met Lys Lys Ala Leu Lys Leu Leu Lys Thr
        140                 145                 150

GAA TTG TAAAGAAAAA AAATCTCCAA GCCCTTCTGT CTGTCAGGCC TTGAGACTTG        645
Glu Leu
    155

AAACCAGAAG AAGTGTGAGA AGACTGGCTA GTGTGGAAGC ATAGTGAACA CACTGATTAG        705

GTTATGGTTT AATGTTACAA CAACTATTTT TTAAGAAAAA CAAGTTTTAG AAATTTGGTT        765

TCAAGTGTAC ATGTGTGAAA ACAATATTGT ATACTACCAT AGTGAGCCAT GATTTTCTAA        825

AAAAAAAAAT AAATGTTTTG GGGGTGTTCT GTTTTCTCCC AAAAAAAAAA                   875

(2) INFORMATION FOR SEQ ID NO:2:

(i) SEQUENCE CHARACTERISTICS:
         (A) LENGTH: 175 amino acids
         (B) TYPE: amino acid
         (D) TOPOLOGY: linear
```

(ii) MOLECULE TYPE: protein (xi) SEQUENCE DESCRIPTION: SEQ ID NO:2:

```
Met Glu Lys Ile Pro Val Ser Ala Phe Leu Leu Leu Val Ala Leu Ser
-20             -15                 -10                 -5

Tyr Thr Leu Ala Arg Asp Thr Thr Val Lys Pro Gly Ala Lys Lys Asp
                1               5                   10

Thr Lys Asp Ser Arg Pro Lys Leu Pro Gln Thr Leu Ser Arg Gly Trp
            15                  20                  25

Gly Asp Gln Leu Ile Trp Thr Gln Thr Tyr Glu Glu Ala Leu Tyr Lys
        30                  35                  40

Ser Lys Thr Ser Asn Lys Pro Leu Met Ile Ile His His Leu Asp Glu
45                  50                  55                  60

Cys Pro His Ser Gln Ala Leu Lys Lys Val Phe Ala Glu Asn Lys Glu
                65                  70                  75

Ile Gln Lys Leu Ala Glu Gln Phe Val Leu Leu Asn Leu Val Tyr Glu
            80                  85                  90

Thr Thr Asp Lys His Leu Ser Pro Asp Gly Gln Tyr Val Pro Arg Ile
        95                  100                 105

Met Phe Val Asp Pro Ser Leu Thr Val Arg Ala Asp Ile Thr Gly Arg
    110                 115                 120

Tyr Ser Asn Arg Leu Tyr Ala Tyr Glu Pro Ala Asp Thr Ala Leu Leu
125                 130                 135                 140

Leu Asp Asn Met Lys Lys Ala Leu Lys Leu Leu Lys Thr Glu Leu
                145                 150                 155
```

(2) INFORMATION FOR SEQ ID NO:3:

(i) SEQUENCE CHARACTERISTICS:
        (A) LENGTH: 1423 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 88..603

(ix) FEATURE:
        (A) NAME/KEY: mat_peptide
        (B) LOCATION: 157..603

(ix) FEATURE:
        (A) NAME/KEY: sig_peptide
        (B) LOCATION: 88..156

(xi) SEQUENCE DESCRIPTION: SEQ ID NO:3:

```
GAGCGGCGCT CGGCGAACTG TGTGGACCGT CTGCTGGGAC TCCGGCCCTG CGTCCGCTCA      60

GCCCCGTGGC CCCGCGCACC TACTGCC ATG GAG ACG CGG CCT CGT CTC GGG         111
                              Met Glu Thr Arg Pro Arg Leu Gly
                              -23             -20

GCC ACC TGT TTG CTG GGC TTC AGT TTC CTG CTC CTC GTC ATC TCT TCT       159
Ala Thr Cys Leu Leu Gly Phe Ser Phe Leu Leu Leu Val Ile Ser Ser
-15                 -10                 -5                   1

GAT GGA CAT AAT GGG CTT GGA AAG GGT TTT GGA GAT CAT ATT CAT TGG       207
Asp Gly His Asn Gly Leu Gly Lys Gly Phe Gly Asp His Ile His Trp
                5                   10                  15

AGG ACA CTG GAA GAT GGG AAG AAA GAA GCA GCT GCC AGT GGA CTG CCC       255
Arg Thr Leu Glu Asp Gly Lys Lys Glu Ala Ala Ala Ser Gly Leu Pro
```

```
                     20                  25                      30
CTG ATG GTG ATT ATT CAT AAA TCC TGG TGT GGA GCT TGC AAA GCT CTA        303
Leu Met Val Ile Ile His Lys Ser Trp Cys Gly Ala Cys Lys Ala Leu
         35                  40                  45

AAG CCC AAA TTT GCA GAA TCT ACG GAA ATT TCA GAA CTC TCC CAT AAT        351
Lys Pro Lys Phe Ala Glu Ser Thr Glu Ile Ser Glu Leu Ser His Asn
 50                  55                  60                  65

TTT GTT ATG GTA AAT CTT GAG GAT GAA GAG GAA CCC AAA GAT GAA GAT        399
Phe Val Met Val Asn Leu Glu Asp Glu Glu Glu Pro Lys Asp Glu Asp
                 70                  75                  80

TTC AGC CCT GAC GGG GGT TAT ATT CCA CGA ATC CTT TTT CTG GAT CCC        447
Phe Ser Pro Asp Gly Gly Tyr Ile Pro Arg Ile Leu Phe Leu Asp Pro
             85                  90                  95

AGT GGC AAG GTG CAT CCT GAA ATC ATC AAT GAG AAT GGA AAC CCC AGC        495
Ser Gly Lys Val His Pro Glu Ile Ile Asn Glu Asn Gly Asn Pro Ser
         100                 105                 110

TAC AAG TAT TTT TAT GTC AGT GCC GAG CAA GTT GTT CAG GGG ATG AAG        543
Tyr Lys Tyr Phe Tyr Val Ser Ala Glu Gln Val Val Gln Gly Met Lys
 115                 120                 125

GAA GCT CAG GAA AGG CTG ACG GGT GAT GCC TTC AGA AAG AAA CAT CTT        591
Glu Ala Gln Glu Arg Leu Thr Gly Asp Ala Phe Arg Lys Lys His Leu
130                 135                 140                 145

GAA GAT GAA TTG TAACATGAAT GTGCCCCTTC TTTCATCAGA GTTAGTGTTC            643
Glu Asp Glu Leu

TGGAAGGAAA GCAGCAGGGA AGGGAATATT GAGGAATCAT CTAGAACAAT TAAGCCGACC      703

AGGAAACCTC ATTCCTACCT ACACTGGAAG GAGCGCTCTC ACTGTGGAAG AGTTCTGCTA      763

ACAGAAGCTG GTCTGCATGT TTGTGGATCC AGCGGAGAGT GGCAGACTTT CTTCTCCTTT      823

TCCCTCTCAC CTAAATGTCA ACTTGTCATT GAATGTAAAG AATGAAACCT TCTGACACAA      883

AACTTGAGCC ACTTGGATGT TTACTCCTCG CACTTAAGTA TTTGAGTCTT TTCCCATTTC      943

CTCCCACTTT ACTCACCTTA GTGGTGAAAG GAGACTAGTA GCATCTTTTC TACAACGTTA     1003

AAATTGCAGA AGTAGCTTAT CATTAAAAAA CAACAACAAC AACAATAACA ATAAATCCTA     1063

AGTGTAAATC AGTTATTCTA CCCCCTACCA AGGATATCAG CCTGTTTTTT CCCTTTTTTC     1123

TCCTGGGAAT AATTGTGGGC TTCTTCCCAA ATTTCTACAG CCTCTTTCCT CTTCTCATGC     1183

TTGAGCTTCC CTGTTTGCAC GCATGCGTGT GCAGGACTGG CTGTGTGCTT GGACTCGGCT     1243

CCAGGTGGAA GCATGCTTTC CCTTGTTACT GTTGGAGAAA CTCAAACCTT CAAGCCCTAG     1303

GTGTAGCCAT TTTGTCAAGT CATCAACTGT ATTTTTGTAC TGGCATTAAC AAAAAAAGAG     1363

ATAAAATATT GTACCATTAA ACTTTAATAA AACTTTAAAA GGAAAAAAAA AAAAAAAAA      1423

(2) INFORMATION FOR SEQ ID NO:4:

(i) SEQUENCE CHARACTERISTICS:
        (A) LENGTH: 172 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Thr Arg Pro Arg Leu Gly Ala Thr Cys Leu Leu Gly Phe Ser
-23                 -20                 -15                 -10

Phe Leu Leu Leu Val Ile Ser Ser Asp Gly His Asn Gly Leu Gly Lys
             -5                   1                   5

Gly Phe Gly Asp His Ile His Trp Arg Thr Leu Glu Asp Gly Lys Lys
 10                  15                  20                  25
```

```
Glu Ala Ala Ala Ser Gly Leu Pro Leu Met Val Ile Ile His Lys Ser
                30                  35                  40

Trp Cys Gly Ala Cys Lys Ala Leu Lys Pro Lys Phe Ala Glu Ser Thr
            45                  50                  55

Glu Ile Ser Glu Leu Ser His Asn Phe Val Met Val Asn Leu Glu Asp
        60                  65                  70

Glu Glu Glu Pro Lys Asp Glu Asp Phe Ser Pro Asp Gly Gly Tyr Ile
    75                  80                  85

Pro Arg Ile Leu Phe Leu Asp Pro Ser Gly Lys Val His Pro Glu Ile
90                  95                 100                 105

Ile Asn Glu Asn Gly Asn Pro Ser Tyr Lys Tyr Phe Tyr Val Ser Ala
               110                 115                 120

Glu Gln Val Val Gln Gly Met Lys Glu Ala Gln Glu Arg Leu Thr Gly
           125                 130                 135

Asp Ala Phe Arg Lys Lys His Leu Glu Asp Glu Leu
           140                 145

(2) INFORMATION FOR SEQ ID NO:5:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: cDNA (ix) FEATURE:
         (A) NAME/KEY: CDS
         (B) LOCATION: 49..546

(ix) FEATURE:
         (A) NAME/KEY: mat_peptide
         (B) LOCATION: 118..546

(ix) FEATURE:
         (A) NAME/KEY: sig_peptide
         (B) LOCATION: 49..117

(xi) SEQUENCE DESCRIPTION: SEQ ID NO:5:

CAAGAGCACT GGCCAAGTCA GCTTCTTCTG AGAGAGTCTC TAGAAGAC ATG ATG CTA        57
                                                    Met Met Leu
                                                    -23

CAC TCA GCT TTG GGT CTC TGC CTC TTA CTC GTC ACA GTT TCT TCC AAC       105
His Ser Ala Leu Gly Leu Cys Leu Leu Leu Val Thr Val Ser Ser Asn
-20                 -15                 -10                 -5

CTT GCC ATT GCA ATA AAA AAG GAA AAG AGG CCT CCT CAG ACA CTC TCA       153
Leu Ala Ile Ala Ile Lys Lys Glu Lys Arg Pro Pro Gln Thr Leu Ser
                 1               5                  10

AGA GGA TGG GGA GAT GAC ATC ACT TGG GTA CAA ACT TAT GAA GAA GGT       201
Arg Gly Trp Gly Asp Asp Ile Thr Trp Val Gln Thr Tyr Glu Glu Gly
            15                  20                  25

CTC TTT TAT GCT CAA AAA AGT AAG AAG CCA TTA ATG GTT ATT CAT CAC       249
Leu Phe Tyr Ala Gln Lys Ser Lys Lys Pro Leu Met Val Ile His His
        30                  35                  40

CTG GAG GAT TGT CAA TAC TCT CAA GCA CTA AAG AAA GTA TTT GCC CAA       297
Leu Glu Asp Cys Gln Tyr Ser Gln Ala Leu Lys Lys Val Phe Ala Gln
    45                  50                  55                  60

AAT GAA GAA ATA CAA GAA ATG GCT CAG AAT AAG TTC ATC ATG CTA AAC       345
Asn Glu Glu Ile Gln Glu Met Ala Gln Asn Lys Phe Ile Met Leu Asn
                65                  70                  75

CTT ATG CAT GAA ACC ACT GAT AAG AAT TTA TCA CCT GAT GGG CAA TAT       393
```

```
Leu Met His Glu Thr Thr Asp Lys Asn Leu Ser Pro Asp Gly Gln Tyr
         80                  85                  90

GTG CCT AGA ATC ATG TTT GTA GAC CCT TCT TTA ACA GTT AGA GCT GAC         441
Val Pro Arg Ile Met Phe Val Asp Pro Ser Leu Thr Val Arg Ala Asp
         95                 100                 105

ATA GCT GGA AGA TAC TCT AAC AGA TTG TAC ACA TAT GAG CCT CGG GAT         489
Ile Ala Gly Arg Tyr Ser Asn Arg Leu Tyr Thr Tyr Glu Pro Arg Asp
        110                 115                 120

TTA CCC CTA TTG ATA GAA AAC ATG AAG AAA GCA TTA AGA CTT ATT CAG         537
Leu Pro Leu Leu Ile Glu Asn Met Lys Lys Ala Leu Arg Leu Ile Gln
125                 130                 135                 140

TCA GAG CTA TAAGAGATGA TAGAAAAAAG CCTTCACTTC AAAGAAGTCA                 586
Ser Glu Leu

AATTTCATGA AGAAAACCTC TGGCACATTG ACAAATACTA AATGTGCAAG TATATAGATT       646

TTGTAATATT ACTATTTAGT TTTTTTAATG TGTTTGCAAT AGTCTTATTA AATAAATGT        706

TTTTTAAAAA AAAAAAAAAA AAAAAA                                            732

(2) INFORMATION FOR SEQ ID NO:6:

(i) SEQUENCE CHARACTERISTICS:
        (A) LENGTH: 166 amino acids
        (B) TYPE: amino acid
        (D) TOPOLOGY: linear (ii) MOLECULE TYPE: protein (xi) SEQUENCE DESCRIPTION: SEQ ID NO:6:

Met Met Leu His Ser Ala Leu Gly Leu Cys Leu Leu Val Thr Val
-23         -20                 -15                 -10

Ser Ser Asn Leu Ala Ile Ala Ile Lys Lys Glu Lys Arg Pro Pro Gln
         -5                   1                   5

Thr Leu Ser Arg Gly Trp Gly Asp Asp Ile Thr Trp Val Gln Thr Tyr
 10                  15                  20                  25

Glu Glu Gly Leu Phe Tyr Ala Gln Lys Ser Lys Lys Pro Leu Met Val
                 30                  35                  40

Ile His His Leu Glu Asp Cys Gln Tyr Ser Gln Ala Leu Lys Lys Val
             45                  50                  55

Phe Ala Gln Asn Glu Glu Ile Gln Glu Met Ala Gln Asn Lys Phe Ile
         60                  65                  70

Met Leu Asn Leu Met His Glu Thr Thr Asp Lys Asn Leu Ser Pro Asp
     75                  80                  85

Gly Gln Tyr Val Pro Arg Ile Met Phe Val Asp Pro Ser Leu Thr Val
 90                  95                 100                 105

Arg Ala Asp Ile Ala Gly Arg Tyr Ser Asn Arg Leu Tyr Thr Tyr Glu
                110                 115                 120

Pro Arg Asp Leu Pro Leu Leu Ile Glu Asn Met Lys Lys Ala Leu Arg
            125                 130                 135

Leu Ile Gln Ser Glu Leu
        140

(2) INFORMATION FOR SEQ ID NO:7:

(i) SEQUENCE CHARACTERISTICS:
        (A) LENGTH: 183 amino acids
        (B) TYPE: amino acid
        (C) STRANDEDNESS: Not Relevant
        (D) TOPOLOGY: linear (ii) MOLECULE TYPE: peptide
```

-continued (xi) SEQUENCE DESCRIPTION: SEQ ID NO:7:

Met Gln Ala Gly Leu Ser Leu Val Cys Leu Val Leu Leu Cys Ser Ala
1               5                   10                  15

Leu Gly Glu Ala Val Leu Lys Lys Pro Lys Gln Ala Gly Thr Thr
            20                  25                  30

Asp Thr Lys Thr Asp Gln Glu Pro Ala Pro Ile Lys Thr Lys Gly Leu
        35                  40                  45

Lys Thr Leu Asp Arg Gly Trp Gly Glu Ser Ile Glu Trp Val Gln Thr
        50                  55                  60

Tyr Glu Glu Gly Leu Ala Lys Ala Arg Glu Asn Asn Lys Pro Leu Met
65                  70                  75                  80

Val Ile His His Leu Glu Asp Cys Pro Tyr Ser Ile Ala Leu Lys Lys
                85                  90                  95

Ala Phe Val Ala Asp Arg Met Ala Gln Lys Leu Ala Gln Glu Asp Phe
            100                 105                 110

Ile Met Leu Asn Leu Val His Pro Val Ala Asp Glu Asn Gln Ser Pro
        115                 120                 125

Asp Gly His Tyr Val Pro Arg Val Ile Phe Ile Asp Pro Ser Leu Thr
    130                 135                 140

Val Arg Ser Asp Leu Lys Gly Arg Tyr Gly Asn Lys Met Tyr Ala Tyr
145                 150                 155                 160

Asp Ala Asp Asp Ile Pro Glu Leu Ile Thr Asn Met Lys Lys Ala Lys
                165                 170                 175

Ser Phe Leu Lys Thr Glu Leu
            180

(2) INFORMATION FOR SEQ ID NO:8:

(i) SEQUENCE CHARACTERISTICS:
        (A) LENGTH: 170 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

Met Glu Xaa Xaa Xaa Xaa Leu Gly Ala Cys Leu Leu Val Ala Leu
1               5                   10                  15

Ser Xaa Xaa Leu Ala Xaa Xaa Xaa Lys Gly Lys Asp Xaa Arg Pro Ile
            20                  25                  30

Lys Gly Pro Gln Thr Leu Ser Arg Gly Trp Gly Asp Xaa Ile Xaa Trp
        35                  40                  45

Val Gln Thr Tyr Glu Glu Gly Leu Xaa Lys Ala Xaa Xaa Ser Asn Lys
        50                  55                  60

Pro Leu Met Val Ile His His Leu Glu Asp Cys Pro Tyr Ser Gln Ala
65                  70                  75                  80

Leu Lys Lys Val Phe Ala Glu Asn Xaa Glu Ile Gln Glu Leu Ala Gln
                85                  90                  95

Asn Phe Val Met Leu Asn Leu Val His Glu Thr Thr Asp Glu Asn Leu
            100                 105                 110

Ser Pro Asp Gly Gln Tyr Val Pro Arg Ile Met Phe Val Asp Pro Ser
        115                 120                 125

Leu Thr Val Arg Ala Asp Ile Xaa Gly Arg Tyr Gly Asn Arg Leu Tyr
    130                 135                 140

```
    Ala Tyr Glu Pro Xaa Asp Xaa Pro Leu Leu Ile Xaa Asn Met Lys Lys
    145                 150                 155                 160

Ala Leu Lys Leu Leu Lys Thr Glu Leu Xaa
                    165                 170

(2) INFORMATION FOR SEQ ID NO:9:

(i) SEQUENCE CHARACTERISTICS:
        (A) LENGTH: 489 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

AATTCGGCAN AGGATCCTAG CCGCCGACTC ACACAAGGCA GAGTTGCCAT GGAGAAAATT     60

CCAGTGTCAG CATTCTTGCT CCTTGTGGCC CTCTCCTACA CTCTGGCCAG AGATACCACA    120

GTCAAACCTG GAGCCAAAAA GGACACAAAG GACTTTCGAC CCAAACTGCC CCAGACCCTC    180

TCCAGAGGTT GGGGTGACCA ACTTCATCTG GACTCAGACA TATGAAGAAG CTCTTATATN    240

AAATCCAAGA CAAGCAACAA ACCCTTGATG ATTATTCATC ACTTGGGTGA GTGCCCACAC    300

AGTTCAAGTT TTTAAAGAAA GTGTTTNGCT GGAAATTAAN GAANTCCGGN AATTGGGNNG    360

AGCAGTTTGT NCCCCNTNAA TTTGGGTTTT GGAAACAATG GGCAAACACC TTTTTTGTTG    420

NTGGNCNATT TTTCCCCGGN TTTTTTTTTT TGGCCCCTTT TTNNAANTTA NGGGCGGTTT    480

TCATGGGGG                                                            489

(2) INFORMATION FOR SEQ ID NO:10:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

AATTCGGCAN AGGAAGACAA GCAACAAACC CTTGATGATT ATTCATCANT TGGATGAGTG     60

CCCACACAGT CAAGCTTTAA AGAAAGTGTT TGCTGAAAAT AAAGAAATCC AGAAATTGGC    120

AGAGCAGTTT GTCCTCCTCA ATCTGGTTTA TGAAACAACT GGACAAACAC CTTTCTCCTG    180

ATGGCCAGTA TGTNCCCAGG GTTATGTTTG TTGACCCATN TCTGGACAGT TAGAGCCGAT    240

ATCACTGGGA GGATATTTCA AACCGTNNCT TATGCTTACG GAACCTGGCA GGTTACAGGT    300

CTGTTTGCTT GGACCAACAT GNAGGAAAGG TTCTTCAAGT TTGGTTGNAN GGACTGGAAT    360

TTGTTNAAGG NANNAAAATT TTTCCAAGGC CTTTTGNTCT TGTTTAAGGN CTTNGGGGTT    420

TTGGAAACCC GNAGGAGNTG TTNAGAAGGA CTTGGTTAGT GTTGGGAGGC CNTNGTGGAA    480

CCCANTGGTT TNGGGTATGG GTTTAA                                         506

(2) INFORMATION FOR SEQ ID NO:11:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:11:

ATTCGGAGAG CCATCTCTGA CAGTTAGAGC CGATATCACT GGAAGATATT CAATCGTCTC     60

TATGCTTACG ACCTGCAGAT ACAGTCTGTT NTTNCACATG AAGAAAGTCT CAAGTTGCTG    120

AAGACTGAAT TGTAAGAAAA ATCTCCAGCC CTTCTGTCTG CAGCTTGAGA CTTGAACCAG    180

AGAGTGTGAG AGCTGCTGTT GGAGNTAGTG ACNATGTTAG GTTGGTATGT ACACACTTTT    240

TTAGAACAGT TTGATTGGTC AGNTCNGGTA ACATTTTTCT CCTGGGCTGT TCAAAAAAAA    300

TGTNGGGTTC TTTCCCAAAA AAAAAAANG                                     329

(2) INFORMATION FOR SEQ ID NO:12:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATTCGGAGAG CCATCTCTGA CAGTTAGAGC CGATATCACT GGAAGATATT CAATCGTCTC     60

TATGCTTACG ACCTGCAGAT ACAGTCTGTT NTTNCACATG AAGAAAGTCT CAAGTTGCTG    120

AAGACTGAAT TGTAAGAAAA ATCTCCAGCC CTTCTGTCTG CAGCTTGAGA CTTGAACCAG    180

AGAGTGTGAG AGCTGCTGTT GGAGNTAGTG ACNATGTTAG GTTGGTATGT ACACACTTTT    240

TTAGAACAGT TTGATTGGTC AGNTCNGGTA ACATTTTTCT CCTGGGCTGT TCAAAAAAAA    300

TGTNGGGTTC TTTCCCAAAA AAAAAAANG                                     329

(2) INFORMATION FOR SEQ ID NO:13:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ATTCGGAGAG CCATCTCTGA CAGTTAGAGC CGATATCACT GGAAGATATT CAATCGTCTC     60

TATGCTTACG ACCTGCAGAT ACAGTCTGTT NTTNCACATG AAGAAAGTCT CAAGTTGCTG    120

AAGACTGAAT TGTAAGAAAA ATCTCCAGCC CTTCTGTCTG CAGCTTGAGA CTTGAACCAG    180

AGAGTGTGAG AGCTGCTGTT GGAGNTAGTG ACNATGTTAG GTTGGTATGT ACACACTTTT    240

TTAGAACAGT TTGATTGGTC AGNTCNGGTA ACATTTTTCT CCTGGGCTGT TCAAAAAAAA    300

TGTNGGGTTC TTTCCCAAAA AAAAAAANG                                     329

(2) INFORMATION FOR SEQ ID NO:14:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

ATTCGGAGAG CCATCTCTGA CAGTTAGAGC CGATATCACT GGAAGATATT CAATCGTCTC     60

```
TATGCTTACG ACCTGCAGAT ACAGTCTGTT NTTNCACATG AAGAAAGTCT CAAGTTGCTG      120

AAGACTGAAT TGTAAGAAAA ATCTCCAGCC CTTCTGTCTG CAGCTTGAGA CTTGAACCAG      180

AGAGTGTGAG AGCTGCTGTT GGAGNTAGTG ACNATGTTAG GTTGGTATGT ACACACTTTT      240

TTAGAACAGT TTGATTGGTC AGNTCNGGTA ACATTTTCT CCTGGGCTGT TCAAAAAAA        300

TGTNGGGTTC TTTCCCAAAA AAAAAAANG                                       329

(2) INFORMATION FOR SEQ ID NO:15:

(i) SEQUENCE CHARACTERISTICS:
        (A) LENGTH: 330 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ATTCGGCAGA GCCATCTCTG ACAGTTAGAG CCGATATCAC TGGAAGATAT TCAATCGTCT       60

CTATGCTTAC GACCTGCAGA TACAGTCTGT TNTTNCACAT GAAGAAAGTC TCAAGTTGCT      120

GAAGACTGAA TTGTAAGAAA AATCTCCAGC CCTTCTGTCT GCAGCTTGAG ACTTGAACCA      180

GAGAGTGTGA GAGCTGCTGT TGGAGNTAGT GACNATGTTA GGTTGGTATG TACACACTTT     240

TTTAGAACAG TTTGATTGGT CAGNTCNGGT AACATTTTTC TCCTGGGCTG TTCAAAAAAA     300

ATGTNGGGGT CTTTCCCAAA AAAAAAAANG                                       330

(2) INFORMATION FOR SEQ ID NO:16:

(i) SEQUENCE CHARACTERISTICS:
        (A) LENGTH: 326 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CGGCGCTNGN CGAACTGTGT GGACCGTCTG CTGGGACTCC GGCCCTGCGT CCGCTCAGCC       60

CCGTGGCCCC GCGCACCTAC TGCCATGGAG ACGCGGCCTC GTCTCGGGGC CACCTGTTTG      120

CTGGGCTTCA GTTTCCTGCT CCTCGTCATC TCTTCTGATG GACATAATGG GCTTGGAAAG     180

GGTTTTGGAG ATCATATTCA TTGGAGGACA CTGGAAGATG GGAAGAAAGA AGCAGCTGCC     240

AGTGGACTGC CCCTGATGGT GATTATTCAT AAATCCTGGT GTGGAGCTTN GCAAAGTCTN     300

AAAGCCCAAA TTTGCAGAAT CTANGG                                          326

(2) INFORMATION FOR SEQ ID NO:17:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

NNTTCGGCAN AGCNANCCAG GNNAACCTCA TTCCTACCTA CACTGGAAGG NGCGCTCTCA       60

CTGTGGAAGA NTTCTGCTAA CAGAAGCTGG TCTGCATGTT TNTGGATCCA GCGGAGAGTG      120

GCAGACTTNT TTCTCCTTTT CCCTCTNACC TAAATGTCAA CTTGTCATTG AATGTAAAGA     180
```

```
ATGAAACCTT CTGACACAAA ANTNGAGCCA CTTGGATGTT TACTCCTCGC ACTTAAGTAT      240

TTGANGCTTT NCCCATTTCC TCCCACTTTA CTCACCTTAG TGGTGAAAGG GAGACTAGTA      300

GCATCTTTNN CTACAACGTT AAAAATTGCA GAAGTAGCTT ATNCATGAAA AANCAACAGC      360

AACANCAATT AACAATTAAA TNCCCAAGGG GTAAANNCAG TTATTCTAAN CCCCTAACCA      420

GGGTTATCAG CCNGTTTNTT TCCCNNTTTT TTTCCCGGGN ATAATTGTGG GGNTTNTTNC      480

CAAATTNNTA CANNC                                                      495

(2) INFORMATION FOR SEQ ID NO:18:

(i) SEQUENCE CHARACTERISTICS:
        (A) LENGTH: 505 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AATTCGGCAC GAGCGTGGCC CCGCGCACCT ACTGCCATGG AGACGCGGCC TCGTCTCGGG       60

GCCACCTGTT TGCTGGGCTT CAGTTTCCTG CTCCTCGTCA TCTCTTCTGA TGGACATAAT      120

GGGNTTGGAA AGGGTTTTGG AGATCATATT CATTGGAGGA CACTGGAAGA TGGGAAGAAA      180

GAAGCAGCTG CCAGTGGACT GCCCCTGATG GTGATTATTC ATAAATCCTG GNGTGGAGGT      240

TGCAAAGTCT AAAGCCCAAA TTTGCAGNAT CTACGGAAAT TTCAGAACTC TCCCATAATT      300

TTGGTAATGG TAAATCTTGA GGATGAGGAG GAACCAAAGG TGAAGNTTTA NCCCTTACGG      360

GGGGTATATT CCACGATCCT TTTTCTNGNC CCATGGCAAG TGCATCNGAA TCATCATGGG      420

TTGAACCCAG TTCAGATTTT TTNCANCCGG NANTTCAGGT TAGAGNAGAA GTTNGNTTCC      480

NAAATCGGTT AAGTNCNTTA AGTAG                                           505

(2) INFORMATION FOR SEQ ID NO:19:

(i) SEQUENCE CHARACTERISTICS:
        (A) LENGTH: 302 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

CTCGTGCGTA TAAGAAGCAG CTGCCAGTGG ACTGCCCCTG ATGGTGATTA TTCATAAATC       60

CTGGTGTGGA GCTTGCAAAG TCTAAAGCCC AAATTTGCAG AATCTACGGA AATTTCAGAA      120

CTCTCCCATA ATTTTGTTAT GGTAAATCTT GAGGATGAAG AGGAACCCAA AGATGAAGAT      180

TTCAGCCCTG ACGGGGGTTA TATTCCACGA ATCCTTTTTC TGGATCCCAG TGGCAAGGTG      240

CATNCTGAAA TCATCAATGA GAATGGAAAC CCCAGCTACA AGTATTTTTT ATTTCAGTGC      300

CG                                                                    302

(2) INFORMATION FOR SEQ ID NO:20:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:20:

```
GGCACGAGGG NAACCCCAGC TACAAGTATT TTTATGTCAG TCCCGAGCAA GTTGTTCAGG      60
GGATGAAGGA AGCTCAGGAA AGGCTGACGG GTGATGCCTT CAGAANGAAA CATCTTGAAG     120
CATAAATTGT AACATGAATG TNCCCCTTCT TTCATCAGAG TTAGTGTTCT GGAAGGAAAG     180
CAGCAGGGGN AGGGAATATT GAGGAATCAT CTAGAACAAT TAAGCCGACC AGGAAACCTN     240
ATTCCTACCT ACACTGGGAN GGAGCGCTCT TCACTGTGGA AGGAGTTTCG GCTAACCAGA     300
AGCTTGGTTC TGNCATGGTT TTGNTGGGAT NCCAGCGGAN GAGTGGG                   347
```

(2) INFORMATION FOR SEQ ID NO:21:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
GGCAGAGGTA AACCCCAGCT ACAAGTATTT TTATGTCAGT NCCGAGCAAG TTGTTCAGGG      60
GATGAAGGAA GCTCAGGAAA GGCTGACGGG TGATGCCTTC AGAANGAAAC ATCTTGAAGA     120
NNNATTGTAA CATGGAATGT GCCCCTTCTT TCATCAGAGT TAGTGTTCTG GAAGGAAAG      180
CAGCAGGGTT AGGGNATATT GAGGAATCAT CTAGAACAAT TAAAGCCGAC CAGGAAACCT     240
CATTNCTACC TACACTGGGA AGGAGCGCTC TCACTGTGNG AAGAGTTCCG GCTTAACAGN     300
AGCTNGGTTC TGNCATGTTT TG                                              322
```

(2) INFORMATION FOR SEQ ID NO:22:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

```
TAATGGACAT AATGGGCTTG GAAAGGNTTT TGGAGATCAT ATTCATTGGA GGACACTGGA      60
AGATGGGAAG AAAGAAGCAG CTGCCAGTGG ACTGCCCCTN ATGGTGATTA TNCATAANTC     120
CTGGTGTGGA GCTTGCAAAG CTCTTAAAGC CCAAATTTNC AGAATCTACG GAAATTTCAG     180
AACTNTCCCA TAATTTNTTA ATGGTAAATC TTGAGGATGA AGAGG                     225
```

(2) INFORMATION FOR SEQ ID NO:23:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
CGCCCATGGG CCAGAGATAC CACAG                                            25
```

(2) INFORMATION FOR SEQ ID NO:24:

(i) SEQUENCE CHARACTERISTICS:

(A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

CGCAAGCTTT TACAATTCAG TCTTCAGC                                           28

(2) INFORMATION FOR SEQ ID NO:25:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GACCGCACAT GTTCTGATGG ACATAATGGG CTTGGAAAGG GTTTTG                       46

(2) INFORMATION FOR SEQ ID NO:26:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GACCGCAAGC TTCTCTGATG AAAGAAGGGG CACATTCTTA TTACAATTC                    49

(2) INFORMATION FOR SEQ ID NO:27:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GACCGCTCAT GAATAAAAAA GGAAAAGAGG CCTCCTCAGA CACTC                        45

(2) INFORMATION FOR SEQ ID NO:28:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GACCGCAAGC TTCTTTGAAG TGAAGGCTTT TTTCTATCAT TTATTATAG                    49

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear

```
        (ii) MOLECULE TYPE: cDNA (xi) SEQUENCE DESCRIPTION: SEQ ID NO:29:

CGCGGATCCG CCATCATGGA GAAAATTCCA GTG                                      33

(2) INFORMATION FOR SEQ ID NO:30:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:30:

CGCGGATCCT TACAATTCAG TCTTCAGC                                            28

(2) INFORMATION FOR SEQ ID NO:31:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:31:

GACTTGATCA GCCATCATGG AGACGCGGCC TCGTCTCGGG GCCACCTG                      48

(2) INFORMATION FOR SEQ ID NO:32:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:32:

GACTGGTACC GAAGGGGCAC ATTCATGTTA CAATTCATCT TCAAG                         45

(2) INFORMATION FOR SEQ ID NO:33:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:33:

GACTGGATCC GCCATCATGA TGCTACACTC AGCTTTGGGT CTCTGCCTC                     49

(2) INFORMATION FOR SEQ ID NO:34:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:34:
```

GACTGGTACC GAAGGCTTTT TTCTATCATC TCTTATAGCT CCTCATATG          49

(2) INFORMATION FOR SEQ ID NO:35:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

TCGACAGGAC ACAAAGGACT CTCGACCCAA ACTGCCCCAG ACCCTCTCCA GAGGTTGGGG          60

TGACAACTCA TCTGGACTCA GACATATGAA GAAGCTCTAT ATAAATCCAA GACAAGCAAC          120

AAACCCTTGA TGATTATTCA TCACTTGGAT GAGTGCCCAC ACAGTCAAGC TTTAAAGAAA          180

GTGTTTGCTG AAAATAAAGA AATCCAGAAA TTGGCAGAGC AGTTTGTCCT CCTCAATCTG          240

GTTTATGAAA CAACTGACAA ACACCTTTCT CCTGATGGCC AGTATGTCCC CAGGATTATG          300

TTTGTTGACC CATCTCTGAC AGTTAGAGCC GATATCACTG GAAGATATTC AAATCGTCTC          360

TATGCTTACG AACCTGCAGA TACAGC                                              386

(2) INFORMATION FOR SEQ ID NO:36:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

AGCCGCCGAC TCACACAAGG CAGGTGGGTG AGGAAATCCA GAGTTGCCAT GGAGAAAATT          60

CCAGTGTCAG CATTCTTGCT CCTTGTGGCC CTCTCCTACA CTCTGGCCAG AGATACCACA          120

GTCAAACCTG GAGCCAAAAA GGACACAAAG GACTCTCGAC TAAAACTGCC CCAGACCCTC          180

TCCAGAGGTT GGGGTGACCA ACTCATCTGG ACTCAGACAT ATGAAGAAGC TCTATATAAA          240

TCCAAGACAN GGCAACAAAC CCTTGATGAT TATTCATCAC TTGGGATGAG TGCCCACACA          300

GTTCANGTTT TTAAGGAAA GTTTTTTNTT GGAAATTTAA GGGAATTNCC GGGAATTGGG           360

CAGGGCAGTT TTT                                                            373

(2) INFORMATION FOR SEQ ID NO:37:

(i) SEQUENCE CHARACTERISTICS:
        (A) LENGTH: 158 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

NCACTCCTAG CCGCCGACTC ACACAAGGCA GGTGGGTGAG GAAATCCAGA GTTGCCATGG          60

AGAAAATTCC AGTGTCAGCA TTCTTGCTCC TTGTGGCCCT CTCCTACACT CTGGCCAGAG          120

ATACCACAGT CAAACCTGGA GCCAAAAAGG ACACAAAG                                 158

(2) INFORMATION FOR SEQ ID NO:38:

```
     (i) SEQUENCE CHARACTERISTICS:
          (A) LENGTH: 136 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:38:

CCCGCATCCT AGCCGCCGAC TCACACAAGG CAGGTGGGTG AGGAAATCCA GAGTTGCCAT      60

GGAGAAAATT CCAGTGTCAG CATTCTTGCT CCTTGTGGCC TCTCCTACAC TCTGGCAGAG     120

ATACCACAGT CAAACT                                                    136

(2) INFORMATION FOR SEQ ID NO:39:

(i) SEQUENCE CHARACTERISTICS:
          (A) LENGTH: 123 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:39:

NNNTNTGGAG AAAACAGAAC ACCCCCAAAA CATTTATTTT TTTTTTTAGA AAATCAGGCT      60

CACTATGGTA GTATACAATA TTGTTTTCAC ACATGTACAC TTGAAACCAA ATTTCAAAAC     120

TTG                                                                  123

(2) INFORMATION FOR SEQ ID NO:40:

(i) SEQUENCE CHARACTERISTICS:
          (A) LENGTH: 311 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:40:

TAATAAGACT ATTGCAAACA CATTAAAAAA ACTAAATAGT AATATTACAA AATCTATATA      60

CTTGCACATT TAGTATTTGT CAATGTGCCA GAGGTTTTCT TCATGAAATT TGACTTCTTT     120

GAAGTGAAGG CTTTTTTCTA TCATCTCTTA TAGCTCTGAC TGAATAAGTC TTAATGCTTT     180

CTTCATGTTT TCTATCAATA GGGGAAATCC CGAGGCTCAT ATGTGNACAA TCTGTTAGAG     240

NATCTCCAGC TATGTCAGCT CTAACTGTTA AAGAGGGTCT ACAAACATGA TTCTAGGGAC     300

ATATTGCCAT C                                                         311

(2) INFORMATION FOR SEQ ID NO:41:

(i) SEQUENCE CHARACTERISTICS:
          (A) LENGTH: 310 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:41:

AGCACTGGCC AAGTCAGCTT CTTCTGAGAG AGTCTCTAGA AGACATGATG CTACACTCAG      60

CTTTGGGTCT CTGCCTCTTA CTCGTCACAG TTTCTTCCAA CCTTGCCATT GCAATAAAAA     120

AGGAAAAGAG GCCTCCTCAG ACACTCTCAA GAGGATGGGG AGATGACATC ACTTGGGTAC     180
```

```
AAACTTATGA AGAAGGTCTC TTTTATGCTC AAAAAAGTAA GGAAGCCATT AATGGGTTAT        240

TCATCACCTG GGGGGANTTG TCAATACTCT TCAAGGCACT TAAAGGNAAG TATTTTGCCC        300

CAAAATTGAA                                                              310
```

(2) INFORMATION FOR SEQ ID NO:42:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

```
GACCGCTCAT GAGAGATACC ACAGTCAAAC CTGGAGCCAA AAAG                         44
```

(2) INFORMATION FOR SEQ ID NO:43:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

```
GACCGCAAGC TTGAAGGGCT TGGAGATTTT TTTTTATTAC AATTC                        45
```

(2) INFORMATION FOR SEQ ID NO:44:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

```
GACTGGATCC GCCATCATGG AGAAAATTCC AGTGTCAGCA TTCTTGCTC                    49
```

(2) INFORMATION FOR SEQ ID NO:45:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

```
GACTGGTACC GGAGATTTTT TTTCTTTACA ATTCAGTCTT CAG                          43
```